US010538475B2

(12) United States Patent
Sittiwong et al.

(10) Patent No.: US 10,538,475 B2
(45) Date of Patent: Jan. 21, 2020

(54) AMPHIPHILIC CYCLOBUTENES AND CYLOBUTANES

(71) Applicant: NUtech Ventures, Lincoln, NE (US)

(72) Inventors: Wantanee Sittiwong, Lincoln, NE (US); Patrick H. Dussault, Lincoln, NE (US); Raul Barletta, Lincoln, NE (US); Robert Powers, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 180 days.

(21) Appl. No.: 14/403,763

(22) PCT Filed: May 28, 2013

(86) PCT No.: PCT/US2013/042897
§ 371 (c)(1),
(2) Date: Nov. 25, 2014

(87) PCT Pub. No.: WO2013/181155
PCT Pub. Date: Dec. 5, 2013

(65) Prior Publication Data
US 2015/0175519 A1    Jun. 25, 2015

Related U.S. Application Data

(60) Provisional application No. 61/651,752, filed on May 25, 2012, provisional application No. 61/702,782, filed on Sep. 19, 2012.

(51) Int. Cl.
| | | |
|---|---|---|
| C07C 59/21 | (2006.01) | |
| C07C 59/205 | (2006.01) | |
| C07C 59/11 | (2006.01) | |
| C08F 232/04 | (2006.01) | |
| C07C 53/134 | (2006.01) | |
| C07C 51/09 | (2006.01) | |
| C07C 57/26 | (2006.01) | |
| C07C 67/313 | (2006.01) | |
| C08F 132/04 | (2006.01) | |
| C08F 212/08 | (2006.01) | |
| C08F 216/16 | (2006.01) | |

(52) U.S. Cl.
CPC .............. *C07C 59/21* (2013.01); *C07C 51/09* (2013.01); *C07C 53/134* (2013.01); *C07C 57/26* (2013.01); *C07C 59/11* (2013.01); *C07C 59/205* (2013.01); *C07C 67/313* (2013.01); *C08F 132/04* (2013.01); *C08F 212/08* (2013.01); *C08F 216/165* (2013.01); *C08F 232/04* (2013.01)

(58) Field of Classification Search
CPC ........ C07C 59/11; C07C 59/205; C07C 59/21
See application file for complete search history.

(56) References Cited

U.S. PATENT DOCUMENTS

| | | | |
|---|---|---|---|
| 4,216,172 A | 8/1980 | Heine et al. | |
| 4,522,811 A | 6/1985 | Eppstein | |
| 6,642,398 B2 * | 11/2003 | Belliotti | ................ C07C 229/08 554/103 |
| 7,964,624 B1 | 6/2011 | Cottrell et al. | |
| 2007/0015758 A1 | 1/2007 | Baruh et al. | |
| 2009/0118287 A1 | 5/2009 | Mogi et al. | |

FOREIGN PATENT DOCUMENTS

| | | |
|---|---|---|
| GB | 1121413 | 7/1968 |
| JP | 06-116198 | 4/1994 |
| WO | WO 99/12881 | 3/1999 |
| WO | WO 2002/058704 | 8/2002 |
| WO | WO 2004/024159 | 3/2004 |
| WO | WO 2010/026214 | 3/2010 |

OTHER PUBLICATIONS

Alberman et al. "Experiments in the cycloButane Series" Journal of the Chemical Society, 1951, pp. 779-782.*
Mahindroo et al. CAS Accession No. 1989:573820.*
Allinger et al. "The Relative Stabilities of cis and frans Isomers. V. The Bicyclo [5.2.0]nonanes. An Extension of the Conformational Rule1,2" Journal of the American Chemical Society, 1960, vol. 81, pp. 4074-4080.*
Hodgetts et al. CAS Accession No. 1994:533560.*
Binns et al. "The preparation and electrocyclic ring-opening of cyclobutenes: Stereocontrolled approaches to substituted conjugated dienes and trienes" Tetrahedron, 1996, vol. 52, No. 10, pp. 3631-3658.*
Barluenga et al. "Reaction of Alkene-Zirconocene Complexes and Cyclic Enol Ethers through New Reaction Pathways" Angewandte Chemie International Edition, 2004, vol. 43, No. 30, pp. 3932-3935.*
Extended European Search Report in European Application No. 13797179.2, dated Apr. 15, 2016, 12 pages.
Frimer et al., "Preparation and Photosensitized Oxidation of Isopropylidenecyclobutanes and-cyclobutenes," The Journal of Organic Chemistry, 1994, 59(4):780-792.
Hemperly, John J., Steven Wolff, and William C. Agosta. "Photochemical formation of 12-methylene-cis-bicyclo [8.2. 0] dodecan-1-ol from 2-methylenecyclododecanone. Restricted rotation in a biradical intermediate." The Journal of Organic Chemistry, 1975, 40(23):3315-3319.
Mahindroo et al., "Ricinoleic Acid to Prostaglandins-III: A Two-carbon Regiospecific Insertion: Synthesis of ( + )-P~ostaglandin E1a,b,c," Indian Journal of Chemistry, 1988, 27B:1080-1089.
Shafiee, et al. "Long-acting contraceptive agents: Cyclopropyl and cyclobutyl esters of norethisterone," Steroids, 1983, 41(3):291-307.

(Continued)

*Primary Examiner* — Joseph R Kosack
(74) *Attorney, Agent, or Firm* — Fish & Richardson P.C.

(57) ABSTRACT

This disclosure relates to amphiphilic compounds containing a cyclobutene or cyclobutane moiety. In some embodiments, the compounds are useful for treating infection by *Mycobacterium* such as *Mycobacterium tuberculosis*. Cyclobutene containing compounds are also useful as monomers in the preparation of amphiphilic polymers.

18 Claims, 4 Drawing Sheets

(56) References Cited

OTHER PUBLICATIONS

Sharma et al., "Chemoinformatic Identification of Novel Inhibitors against Mycobacterium tuberculosis L-aspartate α-decarboxylase," PloS one, 2012, 7(3):e33521.
Block, "Olefin Synthesis by Deoxygenation of Vicinal Diols," Organic Reactions, 1984, DOI: 10.1002/0471264180 or 030.02.
Damaskin, "Adsorpt ion Parameters of Cyclobutane Carboxylic Acid at the Interface of a Mercury Electrode with Aqueous Solutions of O.4M Na2S04 + O.1M H2S04," Russian Journal of Electrochemistry, 2006, 42(9):990-994.
Shi et al., "Ring Opening versus Ring Expansion in Rearrangement of Bicyclic Cyclobutylcarbinyl Radicals," Journal of Organic Chemistry, 73(3):974-982.
Tantirungrotechai, et al., "Assessment of mixed basis set and ONIOM methods on the activation energy of ring opening reactions of substituted cyclobutenes," J of Molecular Structure, 2009, 893(1-3):98-105.
Yu, Xiao-mei, "Study on the Composition of Volatile Oil from Glycyrrhiza uralensis Fisch.by GC-MS," 安徽农业科学 [Journal of Anhui Ag. Sci.], 2010, 2:73-736 [English Abstract].
Baldwin and Belfield, "Specifically deuteriated bicyclo[3.2.0]hepta-2,6-dienes," J. Org. Chem., 52:21, 4772-4776, Oct. 1987.
Baskin et al., "Copper-free click chemistry for dynamic in vivo imaging ," Proc Natl Acad Sci USA, 104:43, 16793-16797, Oct. 2007.
Blackman et al., "Tetrazine Ligation: Fast Bioconjugation Based on Inverse-Electron-Demand Diels—Alder Reactivity," J. Am. Chem. Soc., 130:41, 13518-13519, Oct. 15, 2008.
Blom et al., "Preparative LC-MS Purification: Improved Compound Specific Method Optimization," J. Combi. Chem. 6(6), 874, Nov. 2004.
Devaraj et al., "Fast and sensitive pretargeted labeling of cancer cells through a tetrazine/trans-cyclooctene cycloaddition," Angew Chem Int Ed Engl, 48:36, 7013-6, Dec. 2009.
Devaraj et al., "Tetrazine-Based Cycloadditions: Application to Pretargeted Live Cell Imaging," Bioconjug Chem, 19:12, 2297-2299, Dec. 17, 2008.
Diamandis et al., "The Biotin-(Strept)Avidin System: Principlesand Applicationsin Biotechnology," Clin Chem 37:5, 625-636, May 1991.
Laughlin et al., "In Vivo Imaging of Membrane-Associated Glycans in Developing Zebrafish," Science, 320, 664-667, May 2, 2008.
Link and Tirrell, "Cell Surface Labeling of *Escherichia coli* via Copper(I)-Catalyzed [3+2] Cycloaddition," J Am Chem Soc 125:37:11164-11165, Sep. 17, 2003.
Link et al., "Non-canonical amino acids in protein engineering," Curr Opin Biotechnol 14:6, 603-609, Dec. 2003.
McShane, "Tuberculosis vaccines: beyond bacille Calmette-Guérin ," Phil. Trans. R. Soc. B., 366, 2782-2789, Sep. 2011.
Neef and Schultz, "Selective Fluorescence Labeling of Lipids in Living Cells," Angew Chem Int Ed Engl, 48, 1498-500, Jan. 14, 2009.
Ning et al., "Visualizing Metabolically Labeled Glycoconjugates of Living Cells by Copper-Free and Fast Huisgen Cycloadditions," Angewandte Chemie-International Edition, 47:12, 2253-2255, Mar. 2008.
Peturssion et al., "Protecting Groups in Carbohydrate Chemistry," J. Chem. Educ., 74(11), 1297, Nov. 1997.
Pipkom et al., "Inverse-electron-demand Diels-Alder reaction as a highly efficient chemoselective ligation procedure: Synthesis and function of a BioShuttle for temozolomide transport into prostate cancer cells," J. Pept. Sci., 15, 235-41, Jan. 2009.
Powers et al., "Thermal Chemistry of Bicyclo[4.2.0]oct-2-enes," J. Org. Chem., 72:1, 187-194, Jan. 5, 2007.
Prescher and Bertozzi, "Chemistry in living systems," Nat. Chem Biol, 1, 13-21, Jun. 2005.
Prescher et al., "Chemical remodelling of cell surfaces in living animals," Nature 430:7002, 873-877, Aug. 2004.
Raviglione et al., "Scaling up interventions to achieve global tuberculosis control: progress and new developments," Lancet 379:9829, 1902-1913, May 2012.
Rostovtsev et al., "A Stepwise Huisgen Cycloaddition Process: Copper(I)-Catalyzed Regioselective "Ligation" of Azides and Terminal Alkynes," Angew Chem. Int. Ed 41:14, 2596-2599, Jul. 2002.
Russell et al., "Tuberculosis: What We Don't Know Can, and Does, Hurt Us," Science, 328: 852-856, May 2010.
Wang et al., "Bioconjugation by Copper(I)-Catalyzed Azide-Alkyne [3+2] Cycloaddition," J. Am. Chem. Soc. 125:11 ,3192-3193, Mar. 19, 2003.
Australian Office Action in Australian Application No. 2013267594, dated Nov. 3, 2016, 4 pages.
Kovalenko. "Cyclopropanol approach to the differentiation of the functional groups of malic acid," Vestnik BSU. Series 2: Chemistry. Biology. Geography.—2010, 2: 17-19 (with English translation).
New Zealand Office Action in New Zealand Application No. 702154, dated Aug. 3, 2016, 4 pages.

\* cited by examiner

AMPHIPHILIC CYCLOBUTENES AND CYLOBUTANES

CROSS-REFERENCE TO RELATED APPLICATIONS

This application is a National Stage Application under 35 U.S.C. § 371 and claims the benefit of International Application No. PCT/US2013/042897, filed on May 28, 2013, which claims priority to U.S. application Ser. Nos. 61/651,752, filed on May 25, 2012, and 61/702,782, filed on Sep. 19, 2012, both of the disclosures of which are incorporated by reference in their entireties herein.

TECHNICAL FIELD

This disclosure relates to amphiphilic compounds containing a cyclobutene or cyclobutane moiety. In some embodiments, the compounds are useful for treating infection by *mycobacterium* such as *Mycobacterium tuberculosis*. Cyclobutene containing compounds are also useful as monomers in the preparation of amphiphilic polymers.

BACKGROUND

Tuberculosis resulting from infection by *Mycobacterium tuberculosis* (M. tb) poses a significant disease threat. Based on skin test reactivity, it is estimated that one-third of the world's population has been exposed, resulting annually in approximately nine million cases and 1.4 million deaths (2010 data) (see Raviglione, M. et al. *Lancet* 2012, 379, 1902-1913). The current vaccine, *M. bovis* BCG, yields inconsistent protection and can interfere with diagnostic skin tests. Although numerous candidate vaccines are being tested, their overall safety and efficacy has not been established. Although a number of therapeutic agents have been developed, current treatment regimens require patients to take multiple drugs over a period of months. This, combined with significant drug side effects, commonly results in patient noncompliance leading to relapses and the emergence of drug resistance;[3] a high fraction of active cases involve multi-drug resistant (MDR, XDR) strains.

SUMMARY

It is believed that much of the hardiness and drug resistance of mycobacteria are due to an unusually thick lipid cell wall containing a significant proportion of mycolic acids, a unique class of $C_{54}$-$C_{63}$ branched-chain fatty acids. A number of existing treatments for M. tb, exemplified by isoniazid and ethionamide, inhibit mycolic acid biosynthesis. Mycobacteria incorporate $C_{16}$ and $C_{18}$ fatty acids as biosynthetic feedstocks. The compounds provided herein mimic these feedstocks and the uptake of these specifically functionalized fatty acids is thought to inhibit downstream mycolic acid biosynthesis, leading to virulence-attenuating or even lethal alterations in the mycobacterial cell wall structure.

Provided herein are compounds of Formula (I):

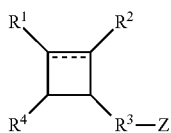

or a pharmaceutically acceptable salt thereof, wherein:
----- represents an optionally present double bond;
$R^1$ and $R^2$ are independently selected from the group consisting of: H, halo, $OR^5$, and =O;
$R^3$ is absent or is an optionally substituted $C_1$-$C_{40}$ alkyl;
$R^4$ is H or an optionally substituted $C_1$-$C_{40}$ alkyl; and
Z is selected from the group consisting of: $COR^6$, $CO_2R^6$, $NHC(O)NR^6R^7$, $CONR^6$, $OCOR^6$, $OR^6$, $SR^6$, $NR^6R^7$, and $OPO_3R^6$;
$R^5$ is H or $C_1$-$C_6$ alkyl;
$R^6$ and $R^7$ are independently H or $C_1$-$C_6$ alkyl;
wherein the hydrocarbon backbone formed by $R^4$ and $R^3$—Z is amphiphilic,
with the proviso that the compound of Formula (I) is not:

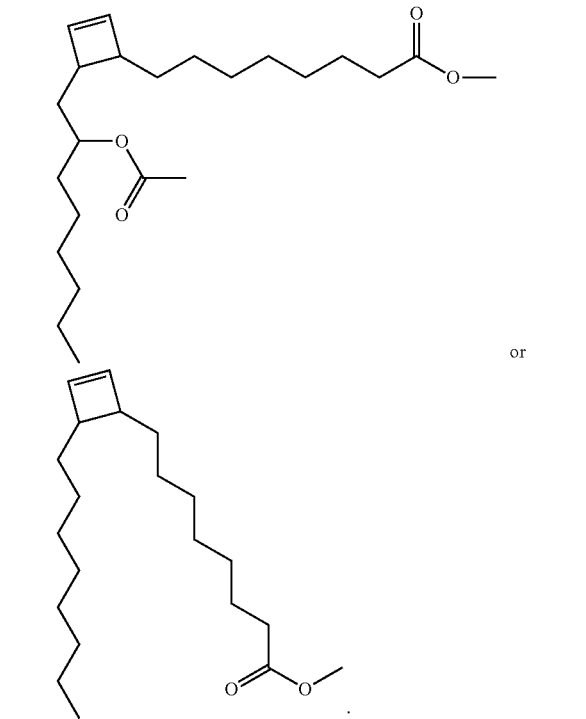

or

In some embodiments, the compound provided herein can be used in a method for treating a mycobacterial infection in a patient, the method comprising administering to the patient a therapeutically effective amount of a compound of Formula (I) or a pharmaceutically acceptable salt thereof. For example, a compound provided herein can be used to treat a mycobacterial infection such as *M. tuberculosis*.

Further provided herein are polymers prepared from a compound of Formula (IV):

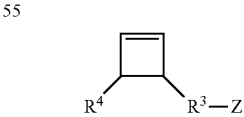

or a pharmaceutically acceptable salt thereof,
wherein:
$R^3$ is absent or is an optionally substituted $C_1$-$C_{40}$ alkyl;
$R^4$ is H or an optionally substituted $C_1$-$C_{40}$ alkyl; and
Z is selected from the group consisting of: $COR^E$, $CO_2R^6$, $NHC(O)NR^6R^7$, $CONR^6$, $OCOR^6$, $OR^6$, $SR^6$, $NR^6R^7$, and $OPO_3R^6$;

$R^5$ is H or $C_1$-$C_6$ alkyl;
$R^6$ and $R^7$ are independently H or $C_1$-$C_6$ alkyl;
wherein the hydrocarbon backbone formed by $R^4$ and $R^3$—Z is amphiphilic.

For example, a compound of Formula (IV) can be prepared by reacting an unsaturated fatty acid or derivative thereof having a backbone comprising at least one carbon-carbon double bond with dihaloketene to achieve a stereospecific cycloaddition across the at least one carbon-carbon double bond, thereby yielding a cycloketone-containing fatty acid derivative comprising a cycloketone along the backbone, wherein the cycloketone comprises at least four carbon atoms, with at least two of the at least four carbon atoms being part of the backbone of the cycloketone-containing fatty acid derivative; reducing the cycloketone-containing fatty acid derivative to yield an amphiphilic cycloalkene-containing fatty acid derivative having a hydrophobic end, a hydrophilic end, and a backbone therebetween comprising a cycloalkene, wherein the cycloalkene comprises at least four carbon atoms, with at least two of the four carbon atoms being part of the backbone of the amphiphilic cycloalkene-containing fatty acid derivative.

In some embodiments, a multiplicity of compounds of Formula (IV) can be polymerized to yield a polymer comprising carbon-carbon double bonds. In some such embodiments, the polymerization can further include hydrogenating the carbon-carbon double bonds of the polymer; cleaving at least some of the carbon-carbon double bonds in the polymer via oxidation to yield monomeric products; cross-linking the amphiphilic cycloalkene-containing fatty acid derivatives via the carbon-carbon double bond in the cycloalkene; ring-opening metathesis reactions; aligning the backbones of the multiplicity of the amphiphilic cycloalkene-containing fatty acid derivatives before polymerizing the multiplicity of the amphiphilic cycloalkene-containing fatty acid derivatives; polymerizing via click-chemistry; and mixtures thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Definitions

Figure 1:
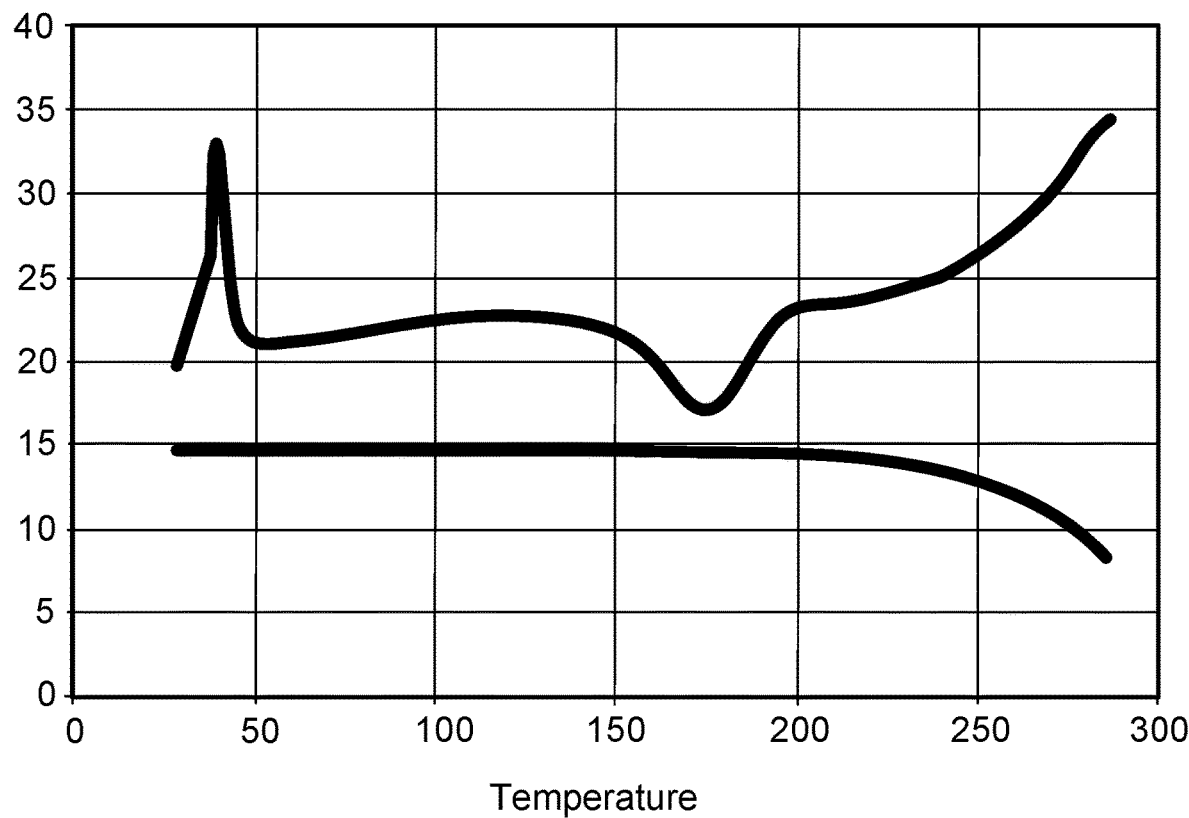
FIG. 1 illustrates the thermal stability of cyclobutene 1. y axis is weight in mg for the lower line and heat flow endo down in mW for top line.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

The term "alkyl" includes straight-chain alkyl groups (e.g., methyl, ethyl, propyl, butyl, pentyl, hexyl, heptyl, octyl, nonyl, decyl, etc.) and branched-chain alkyl groups (e.g., isopropyl, tert-butyl, isobutyl, etc.). In certain embodiments, a straight chain or branched chain alkyl has twelve or fewer carbon atoms in its backbone (e.g., $C_1$-$C_{12}$ for straight chain; $C_3$-$C_{12}$ for branched chain). The term $C_1$-$C_{12}$ includes alkyl groups containing 1 to 12 carbon atoms.

The term "alkenyl" includes aliphatic groups that may or may not be substituted, as described above for alkyls, containing at least one double bond and at least two carbon atoms. For example, the term "alkenyl" includes straight-chain alkenyl groups (e.g., ethenyl, propenyl, butenyl, pentenyl, hexenyl, heptenyl, octenyl, nonenyl, and decenyl) and branched-chain alkenyl groups. In certain embodiments, a straight chain or branched chain alkenyl group has twelve or fewer carbon atoms in its backbone (e.g., $C_2$-$C_{12}$ for straight chain; $C_3$-$C_{12}$ for branched chain). The term $C_2$-$C_{12}$ includes alkenyl groups containing 2 to 12 carbon atoms.

The term "alkynyl" includes unsaturated aliphatic groups analogous in length and possible substitution to the alkyls described above, but which contain at least one triple bond and two carbon atoms. For example, the term "alkynyl" includes straight-chain alkynyl groups (e.g., ethynyl, propynyl, butynyl, pentynyl, hexynyl, heptynyl, octynyl, nonynyl, and decynyl) and branched-chain alkynyl groups. In certain embodiments, a straight chain or branched chain alkynyl group has twelve or fewer carbon atoms in its backbone (e.g., $C_2$-$C_{12}$ for straight chain; $C_3$-$C_{12}$ for branched chain). The term $C_2$-$C_{12}$ includes alkynyl groups containing 2 to 12 carbon atoms.

The term "alkoxy" is used in its conventional sense, and refers to alkyl groups linked to molecules via an oxygen atom. In some embodiments, an alkoxy has twelve or fewer carbon atoms in its backbone (e.g., a $C_1$-$C_{12}$ alkoxy). For example, $C_1$-$C_{10}$, $C_1$-$C_8$, $C_1$-$C_6$, $C_1$-$C_4$, $C_1$-$C_3$, or $C_1$-$C_2$. Non-limiting examples of an alkoxy group include methoxy, ethoxy, propoxy, butoxy, and hexoxy.

The terms "halo" or "halogen", used alone or in combination with other terms, refers to fluoro, chloro, bromo and iodo.

The term "haloalkyl" refers to an alkyl group in which one or more of the hydrogen atoms has been replaced by a halogen atom. The term "$C_n$—$C_m$ haloalkyl" refers to a $C_n$—$C_m$ alkyl group having n to m carbon atoms, and from at least one up to $\{2(n \text{ to } m)+1\}$ halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_n$—$C_m$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "amino" refers to a group of formula —$NH_2$.

The term "carbamyl" refers to a group of formula —C(O)$NH_2$.

The term "carbonyl", employed alone or in combination with other terms, refers to a —C(=O)— group, which also may be written as C(O).

The term "oxo" refers to oxygen as a divalent substituent, forming a carbonyl group, or attached to a heteroatom forming a sulfoxide or sulfone group, or an N-oxide group.

The term "aromatic" refers to a carbocycle or heterocycle having one or more polyunsaturated rings having aromatic character (i.e., having (4n+2) delocalized π (pi) electrons where n is an integer).

The term "carbocyclyl" includes a cyclic aliphatic group which may be saturated or unsaturated. For example, carbocyclyl groups include cyclopropyl, cyclopentyl, cyclohexyl, cycloheptyl, and cyclooctyl. In some embodiments, carbocyclyls have from 3-8 carbon atoms in their ring structure, for example, they can have 3, 4, 5 or 6 carbons in the ring structure.

In general, the term "aryl" includes groups, including 5- and 6-membered single-ring aromatic groups, such as benzene and phenyl. Furthermore, the term "aryl" includes multicyclic aryl groups, e.g., tricyclic, bicyclic, such as naphthalene and anthracene.

The term "heteroaryl" includes groups, including 5- and 6-membered single-ring aromatic groups, that have from one to four heteroatoms, for example, pyrrole, furan, thiophene, thiazole, isothiaozole, imidazole, triazole, tetrazole, pyrazole, oxazole, isooxazole, pyridine, pyraiine, pyridazine, and pyrimidine, and the like. Furthermore, the term "heteroaryl" includes multicyclic heteroaryl groups, e.g., tricyclic, bicyclic, such as benzoxazole, benzodioxazole, benzothiazole, benzoimidazole, benzothiophene, methylenedioxyphenyl, quinoline, isoquinoline, napthyridine, indole, benzofuran, purine, benzofuran, quinazoline, deazapurine, indazole, or indolizine.

The term "heterocyclyl" includes non-aromatic groups, including but not limited to, 3- to 10-membered single or multiple non-aromatic rings having one to five heteroatoms, for example, oxetane, piperazine, pyrrolidine, piperidine, or homopiperazine.

The term "substituted" means that an atom or group of atoms replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position. In some cases, two sites of substitution may come together to form a 3-10 membered carbocyclyl or heterocyclyl ring.

Substituents include, but are not limited to, $Cy^1$, $C_{1-6}$ alkyl, $C_{2-6}$ alkenyl, $C_{2-6}$ alkynyl, halo, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$;

each $Cy^1$ is independently $C_{6-10}$ aryl, $C_{3-10}$ carbocyclyl, 5-10 membered heteroaryl or 4-10 membered heterocyclyl, each of which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$ and oxo;

each $R^{a1}$, $R^{b1}$, $R^{c1}$, $R^{d1}$, is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ carbocyclyl, 5-10 membered heteroaryl, 4-10 membered heterocyclyl, $C_{6-10}$ aryl-$C_{1-4}$ alkyl, $C_{3-10}$ carbocyclyl-$C_{1-4}$ alkyl, (5-10 membered heteroaryl)-$C_{1-4}$ alkyl or (4-10 membered heterocyclyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ carbocyclyl, 5-10 membered heteroaryl, 4-10 membered heterocyclyl, $C_{6-10}$ aryl-$C_{1-4}$ alkyl, $C_{3-10}$ carbocyclyl-$C_{1-4}$ alkyl, (5-10 membered heteroaryl)-$C_{1-4}$ alkyl and (4-10 membered heterocyclyl)-$C_{1-4}$ alkyl is optionally substituted with 1, 2, 3, 4, or 5 substituents independently selected from $C_{1-4}$ alkyl, $C_{1-4}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}NR^{d4}$, $NR^{c4}NR^{d4}$ $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$ and $S(O)_2NR^{c4}R^{d4}$;

each $R^{a4}$, $R^{b4}$, $R^{c4}$ and $R^{d4}$ is independently selected from H, $C_{1-4}$ alkyl, $C_{1-4}$ haloalkyl, $C_{2-4}$ alkenyl and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy.

Where substituent groups are specified by their conventional chemical formulas, written from left to right, they equally encompass the chemically identical substituents that would result from writing the structure from right to left, for example, —$CH_2O$— is equivalent to —$OCH_2$—. In some embodiments, one or more substituents can be a group reactive with a biologically active molecule or a detectable agent.

As used herein, chemical structures which contain one or more stereocenters depicted with dashed and bold bonds (i.e., ⋮ | ) are meant to indicate absolute stereochemistry of the stereocenter(s) present in the chemical structure. As used herein, bonds symbolized by a simple line do not indicate a stereo-preference. Unless otherwise indicated, chemical structures, which include one or more stereocenters, illustrated herein without indicating absolute or relative stereochemistry encompass all possible stereoisomeric forms of the compound (e.g., diastereomers, enantiomers) and mixtures thereof (e.g., racemic mixtures). Structures with a single bold or dashed line, and at least one additional simple line, encompass a single enantiomeric series of all possible diastereomers.

Resolution of racemic mixtures of compounds can be carried out by any of numerous methods known in the art. An exemplary method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "salt" includes any ionic form of a compound and one or more counter-ionic species (cations and/or anions). Salts also include zwitterionic compounds (i.e., a molecule containing one more cationic and anionic species, e.g., zwitterionic amino acids). Counter ions present in a salt can include any cationic, anionic, or zwitterionic species. Exemplary anions include, but are not limited to: chloride, bromide, iodide, nitrate, sulfate, bisulfate, sulfite, bisulfite, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluoromethanesulfonate, ethanesulfonate, benzenesulfonate, p-toluenesulfonate, p-trifluoromethylbenzenesulfonate, hydroxide, aluminates, and borates. Exemplary cations include, but are not limited to: monovalent alkali metal cations, such as lithium, sodium, potassium, and cesium, and divalent alkaline earth metals, such as beryllium, magnesium, calcium, strontium, and barium. Also included are transition metal cations, such as gold, silver, copper and zinc, as well as non-metal cations, such as ammonium salts.

Also provided herein are pharmaceutically acceptable salts of the compounds described herein. As used herein, "pharmaceutically acceptable salts" refers to derivatives of the disclosed compounds wherein the parent compound is modified by converting an existing acid or base moiety to its salt. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; in some embodiments, a non-aqueous media like ether, ethyl acetate, alcohols (e.g., methanol, ethanol, isopropanol, or butanol) or acetonitrile (ACN) can be used. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977). Conventional methods for preparing salts are described, for example, in *Handbook of Pharmaceutical Salts: Properties, Selection, and Use,* Wiley-VCH, 2002.

The term "essentially pure" refers to chemical purity of a compound provided herein that may be substantially or essentially free of other components which normally accompany or interact with the compound prior to purification. By way of example only, a compound may be "essentially pure" when the preparation of the compound contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, an "essentially pure" compound may have a purity level of about 70%, about 75%, about 80%, about 85%, about 90%, about 95%, about 96%, about 97%, about 98%, about 99% or greater. For the purposes of this document, preparations of functionalized polymers or conjugates differing only in the length of their polymer chain are considered to be essentially pure. An essentially pure compound may be obtained using chromatographic purification methods.

As used herein, "amphiphilic" or "amphiphile" refers to a chemical compound possessing regions of very different properties in terms of preferred solvation or association with a liquid interface or a solid surface. The most common examples of amphiphiles possess both hydrophilic (water-loving, polar) and lipid (fat-loving, non-polar) properties. Generally, amphiphilic compounds herein have a polar region on one half or terminal portion of the compound and a non-polar region at the opposite half or terminal portion of the compound. Fatty acids, triglycerides, and derivatives thereof are examples of amphiphilic compounds. An example of another class of amphiphiles are molecules containing either a hydrophobic or hydrophiic region on one half or terminal portion of the molecule and a thiol or similar functional group possessing high affinity for a metal on the other half or terminus.

"Fatty acid derivatives" as used herein refer to compounds having a fatty acid hydrocarbon backbone, but which may be optionally substituted as provided herein. In addition, a fatty acid derivative may have the carboxylic acid functional group replaced with another reactive group, for example, a hydroxyl group, an ester group, an aldehyde group, a carboxyl group, a sulfhydryl group, an amine group, an amide group, a carbamide group, or a phosphate group.

A "therapeutically effective amount" of a compound with respect to the subject method of treatment, refers to an amount of the compound(s) in a preparation which, when administered as part of a desired dosage regimen (to a patient, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a patient's condition.

Antimicrobial Agents

Provided herein are amphiphilic compounds containing a cyclobutane or cyclobutene moiety. For example, amphiphilic acids, alcohols, esters, thiols, amides, or related groups incorporating within their backbone a four-membered ring carbocycle (cyclobutane, cyclobutene, cyclobutanone, or substituted derivatives).

A compound provided herein can include a compound of Formula (I):

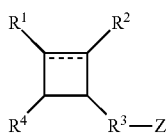

or a pharmaceutically acceptable salt thereof,
wherein:
----- represents an optionally present double bond;
$R^1$ and $R^2$ are independently selected from the group consisting of: H, halo, $OR^5$, and =O;
$R^3$ is absent or is an optionally substituted $C_1$-$C_{40}$ alkyl;
$R^4$ is H or an optionally substituted $C_1$-$C_{40}$ alkyl; and
Z is selected from the group consisting of: $COR^6$, $CO_2R^6$, $NHC(O)NR^6R^7$, $CONR^6$, $OCOR^6$, $OR^6$, $SR^6$, $NR^6R^7$, and $OPO_3R^6$;
$R^5$ is H or $C_1$-$C_6$ alkyl;
$R^6$ and $R^7$ are independently H or $C_1$-$C_6$ alkyl;
wherein the hydrocarbon backbone formed by $R^4$ and $R^3$—Z is amphiphilic In some embodiments, the compound of Formula (I) is not:

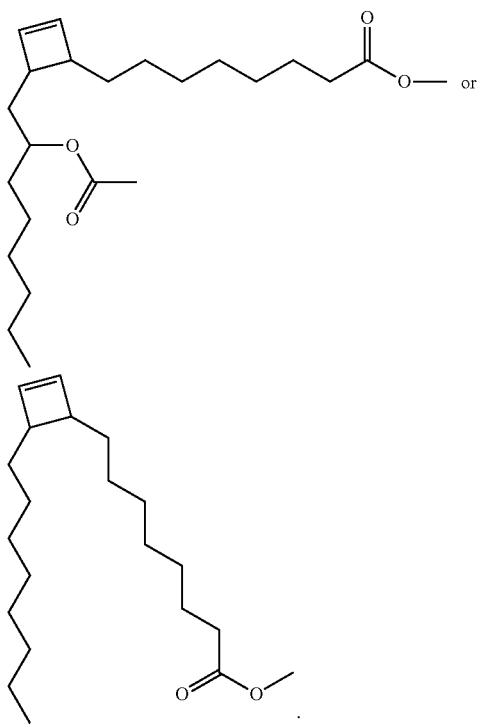

In some embodiments, $R^1$ and $R^2$ are independently selected from the group consisting of: H, halo, OH and =O.

In some embodiments, at least one of $R^3$ or $R^4$ is a $C_1$-$C_{40}$ alkyl. For example, if $R^4$ is H, then $R^3$ is a $C_1$-$C_{40}$ alkyl (e.g., $C_5$-$C_{20}$ alkyl, $C_{10}$$C_{30}$ alkyl, and $C_2$-$C_8$ alkyl), or if $R^3$ is absent, then $R^4$ is $C_1$-$C_{40}$ alkyl (e.g., $C_5$-$C_{20}$ alkyl, $C_{10}$$C_{30}$ alkyl, and $C_2$-$C_8$ alkyl). In some embodiments, $R^3$ is a $C_1$-$C_{10}$ alkyl. For example, $R^3$ can be a $C_7$ alkyl. In some embodiments, $R^4$ is a $C_1$-$C_{10}$ alkyl. For example, $R^4$ can be a $C_8$ alkyl. In some embodiments, $R^4$ is H. $R^3$ and $R^4$ can be independently optionally substituted. For example, substituents include, but are not limited to, $Cy^1$, $C_{1-6}$ alkyl, $C_{2-6}$ alkenyl, $C_{2-6}$ alkynyl, halo, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$;

each $Cy^1$ is independently $C_{6-10}$ aryl, $C_{3-10}$ carbocyclyl, 5-10 membered heteroaryl or 4-10 membered heterocyclyl, each of which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$ and oxo;

each $R^{a1}$, $R^{b1}$, $R^{c1}$, $R^{d1}$, is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ carbocyclyl, 5-10 membered heteroaryl, 4-10 membered heterocyclyl, $C_{6-10}$ aryl-$C_{1-4}$ alkyl, $C_{3-10}$ carbocyclyl-$C_{1-4}$ alkyl, (5-10 membered heteroaryl)-$C_{1-4}$ alkyl or (4-10 membered heterocyclyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ carbocyclyl, 5-10 membered heteroaryl, 4-10 membered heterocyclyl, $C_{6-10}$ aryl-$C_{1-4}$ alkyl, $C_{3-10}$ carbocyclyl-$C_{1-4}$ alkyl, (5-10 membered heteroaryl)-$C_{1-4}$ alkyl and (4-10 membered heterocyclyl)-$C_{1-4}$ alkyl is optionally substituted with 1, 2, 3, 4, or 5 substituents independently selected from $C_{1-4}$ alkyl, $C_{1-4}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$ and $S(O)_2NR^{c4}R^{d4}$;

each $R^{a4}$, $R^{b4}$, $R^{c4}$ and $R^{d4}$ is independently selected from H, $C_{1-4}$ alkyl, $C_{1-4}$ haloalkyl, $C_{2-4}$ alkenyl and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy.

In some embodiments, the substituents can be selected from the group consisting of an alkyl, a halogen, a hydroxyl, an alkoxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a suithydryl, an alkylthio, a sulfate, a sulfonate, a sulfamoyl, a sulfonamido, a sulfonyl, a carbocyclyl, a heterocyclyl, an aralkyl, a heteroaralkyl, or an aromatic or heteroaromatic moiety.

In some embodiments, Z is $CO_2R^6$.

A compound provided herein can be selected from the group consisting of:

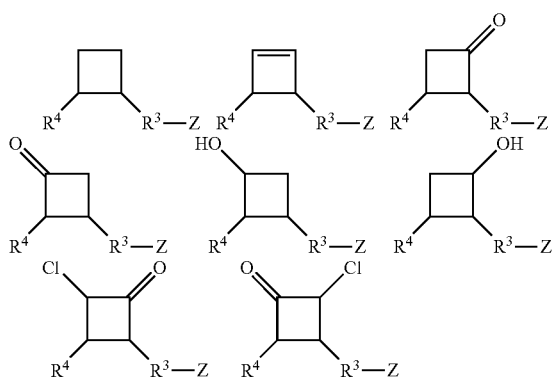

or a pharmaceutically acceptable salt thereof, wherein $R^3$, $R^4$ and Z are as described previously.

In some embodiments, a compound provided herein is a compound of Formula (II):

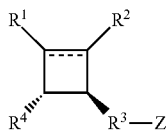

or a pharmaceutically acceptable salt thereof, wherein $R^1$, $R^2$, $R^3$, $R^4$ and Z are as described previously. In some embodiments, a compound provided herein is a compound of Formula (III):

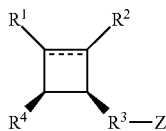

or a pharmaceutically acceptable salt thereof, wherein $R^1$, $R^2$, $R^3$, $R^4$ and Z are as described previously.

Non-limiting examples of a compound provided herein includes:

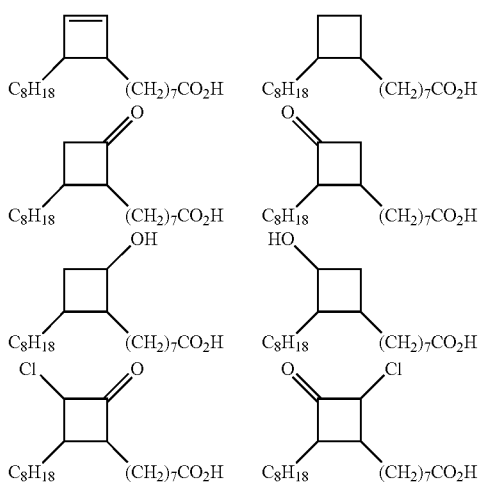

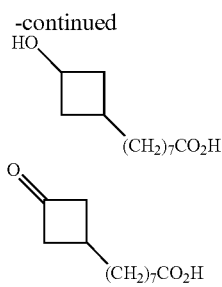

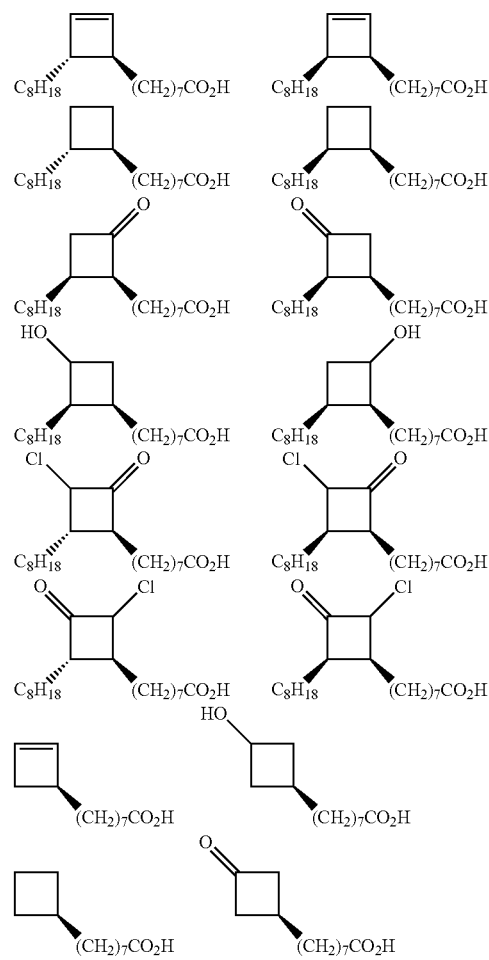

or a pharmaceutically acceptable salt thereof.

In some embodiments, a compound provided herein can be selected from the group consisting of:

or a pharmaceutically acceptable salt thereof.

Pharmaceutical Compositions and Dosage Forms

When employed as pharmaceuticals, the compounds provided herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal, intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also provides pharmaceutical compositions which contain, as the active ingredient, a compound provided herein or a pharmaceutically acceptable salt thereof, in combination with one or more pharmaceutically acceptable carriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, an active compound can be milled to provide the appropriate particle size prior to combining with the other ingredients. If an active compound is substantially insoluble, it can be milled to a particle size of less than 200 mesh. If an active compound is substantially water soluble, the particle size can be adjusted by milling to provide a substantially uniform distribution in the formulation, e.g. about 40 mesh.

The compounds provided herein may be milled using known milling procedures such as wet milling to obtain a particle size appropriate for tablet formation and for other formulation types. Finely divided (nanoparticulate) preparations of the compounds provided herein can be prepared by processes known in the art, e.g., see International App. No. WO 2002/000196.

Some examples of suitable excipients include lactose, dextrose, sucrose, sorbitol, mannitol, starches, gum *acacia*, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions provided herein can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid preformulation composition containing a homogeneous mixture of a compound provided herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient provided herein.

The tablets or pills provided herein can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions provided herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

In some embodiments, the compounds provided herein are for nulated for intravenous administration. Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freezedrying, which yield a powder of the active ingredient plus any additional desired ingredient from a previously sterile-filtered solution thereof.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound provided herein. The topical formulations can be suitably packaged in tubes of, for example, 100 g which are optionally associated with instructions for the treatment of the select indication.

In one embodiment, the compounds provided herein are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions provided herein contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions provided herein contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions provided herein contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses provided herein.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The therapeutic dosage of a compound provided herein can vary according to, for example, the particular use for which the treatment is made, the manner of administration of the compound, the health and condition of the patient, and the judgment of the prescribing physician. The proportion or concentration of a compound provided herein in a pharmaceutical composition can vary depending upon a number of factors including dosage, chemical characteristics (e.g., hydrophobicity), and the route of administration. For example, the compounds provided herein can be provided in an aqueous physiological buffer solution containing about 0.1 to about 10% w/v of the compound for parenteral administration. Some typical dose ranges are from about 1 mg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Methods of Use

The compounds provided herein can be used as antibacterial agents, in particular, antimycobacterial agents. In some embodiments, the bacterial infection is a Gram-positive organism that either uptakes mycolic acid, uses mycolic acid in a biosynthetic process, synthesizes mycolic acid, or requires mycolic acid as a nutritional supplement. For example, the compounds provided herein can used to treat a patient infected with a *mycobacterium*. In some embodiments, the compounds provided herein can inhibit the growth of a *mycobacterium* (e.g., *Mycobacterium tuberculosis*). Accordingly, provided herein is a method for treating a mycobacterial infection in a mammal comprising administering a therapeutically effective amount of a compound provided herein.

Without being bound by any theory, the compounds provided herein are thought to function through selective inhibition or activation of biological processes that would normally process fatty acids, esters, alcohols. In some embodiments, the compounds may function as competitive or irreversible inhibitors based upon their inclusion of, for example, a strained four-membered ring moiety. By way of example, certain mycolic acids are found in the cell wall of *M. tuberculosis*; in particular, α-mycolic acid, which incorporates two cyclopropane rings. The presence of cyclopropanes are thought to contribute to the structural integrity of the cell wall and protect the vacillus from oxidative stress inside macrophages. Mycolic acids are assembled in mycobacteria from shorter-chain fatty acid feedstocks. The compounds provided herein can be taken up into the bacteria my mimicking these feed stocks and can, for example, disrupt mycolic acid biosynthesis through the presence of their strained four-membered ring moieties.

*Mycobacterium* include, for example, bacteria which are members of the groups including *Mycobacterium tuberculosis* complex (MTBC), *Mycobacterium avium* complex (MAC), *Mycobacterium gordonae* clade, *Mycobacterium kansasii* clade, *Mycobacterium nonchromogenicum/terrae* clade, Mycolactone-producing mycobacteria, *Mycobacterium simiae* clade, *Mycobacterium chelonae* clade, *Mycobacterium fortuitum* clade, *Mycobacterium fortuitum* clade, *Mycobacterium parafortuitum* clade, *Mycobacterium vaccae* clade, and CF.

For example, each of the groups include the following bacteria as members:

*Mycobacterium tuberculosis* complex (MTBC) include, for example, *M. tuberculosis, M. bovis, M. bovis* BCG, *M. africanum, M. canetti, M. caprae, M. microti*, and *M. pinnipedii;*

*Mycobacterium avium* complex (MAC) include, for example, *M. avium, M. avium* paratuberculosis, *M. avium* silvaticum, *M. avium* "hominissuis", *M. colombiense*, and *M. indicus* pranii,

*Mycobacterium gordonae* clade include, for example, *M. asiaticumm* and *M. gordonae;*

*Mycobacterium kansasii* clade include, for example, *M. gastri* and *M. kansasii;*

*Mycobacterium nonchromogenicum/terrae* clade include, for example, *M. hiberniae, M. nonchromogenicum, M. terrae, M. triviale*, and Mycolactone-producing mycobacteria;

*Mycobacterium simiae* clade include, for example, *M. triplex, M. genavense, M. florentinum, M. lentiflavum, M. palustre, M. kubicae, M. parascrofulaceum, M. heidelbergense, M. interjectum*, and *M. simiae;*

*Mycobacterium chelonae* clade include, for example, *M. abscessus, M. chelonae*, and *M. bolletii;*

*Mycobacterium fortuitum* clade include, for example, *M. fortuitum, M. fortuitum, M. boenickei, M. peregrinum, M. porcinum, M. senegalense, M. septicum, M. neworleansense, M. houstonense, M. mucogenicum, M. mageritense, M. brisbanense*, and *M. cosmeticum;*

*Mycobacterium parafortuitum* clade include, for example, *M. parafortuitum, M. austroafricanum, M. diernhoferi, M. hodleri, M. neoaurum*, and *M. frederiksbergense;*

*Mycobacterium vaccae* clade include, for example, *M. aurum* and *M. vaccae;*

CF include, for example, *M. chitae* and *M. fallax.*

Additional examples of *mycobacterium* include, for example, *M. branderi, M. cookie, M. celatum, M. bohemicum, M. haemophilum, M. malnloense, M. szulgai, M. leprae, M. lepraemurium, M. lepromatosis, M. africanum, M. botniense, M. chimaera, M. conspicuum, M. doricum, M. farcinogenes, M. heckeshornense, M. intracellulare, M. lacus, M. marinum, M. monacense, M. montefiorense, M. murale, M. nebraskense, M. saskatchewanense, M. scrofulaceum, M. shimoidei, M. tusciae, M. xenopi, M. ulcerans, M. pseudoshottsii, M. shottsii, M. confluentis, M. flavescens, M. madagascariense, M. phlei, M. smegmatis, M. goodii, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense, M. tokaiense*, and *M. intermedium.*

In some embodiments, the *mycobacterium* is a member of MTBC. For example, *M. tuberculosis*, the major cause of human tuberculosis, *M. bovis, M. bovis* BCG, *M. avium*. In some embodiments, the *mycobacterium* is *M. tuberculosis*. In some embodiments, the *mycobacterium* is *M. bovis*. In some embodiments, the *mycobacterium* is *M. avium* subspecies paratuberculosis.

In some embodiments, one or more compounds provided herein are administered with another antibiotic useful for treating mycobacterial infections. These additional antibiotics may include: ethambutol, isoniazid, pyrazinamide, members of the rifamycin class (including, for example, rifampicin), aminoglycosides (for example, amikacin or kanamycin), polypeptides (for example, capreomycin, viomycin, or enviomycin), fluoroquinolones (for example ciprofloxacin levofloxacin, or moxifloxacin), ethionamide, prothionamide, cycloserine, any other antibiotic employed as part of a therapeutic treatment for mycocaterial infections, and any combination of the antibiotics listed above. The additional antibiotic can be administered before, after, or simultaneously with a compound as provided herein.

Amphiphilic Polymers

Certain of the compounds provided herein are can be used as monomers to produce amphiphilic polymers. Such reactions can prepare a variety of polymers such as those shown in Scheme 1.

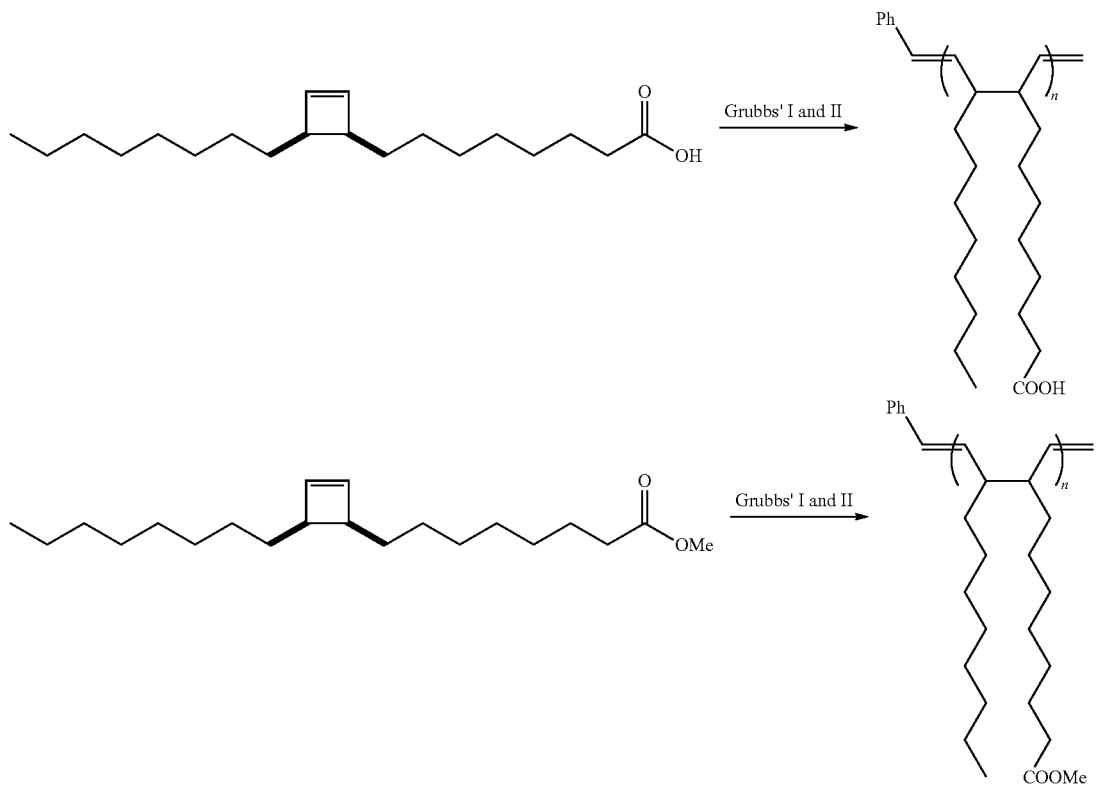

Compounds of Formula (IV) can be used to prepare polymers using any number of known polymerization reactions. A compound of Formula (IV) includes:

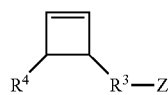

or a pharmaceutically acceptable salt thereof, wherein:

$R^3$ is absent or is an optionally substituted $C_1$-$C_{40}$ alkyl;

$R^4$ is H or an optionally substituted $C_1$-$C_{40}$ alkyl; and

Z is selected from the group consisting of: $COR^E$, $CO_2R^6$, $NHC(O)NR^6R^7$, $CONR^6$, $OCOR^6$, $OR^6$, $SR^6$, $NR^6R^7$, and $OPO_3R^6$;

$R^5$ is H or $C_1$-$C_6$ alkyl;

$R^6$ and $R^7$ are independently H or $C_1$-$C_6$ alkyl;

wherein the hydrocarbon backbone formed by $R^4$ and $R^3$—Z is amphiphilic.

In some embodiments, the compound of Formula (I) is not:

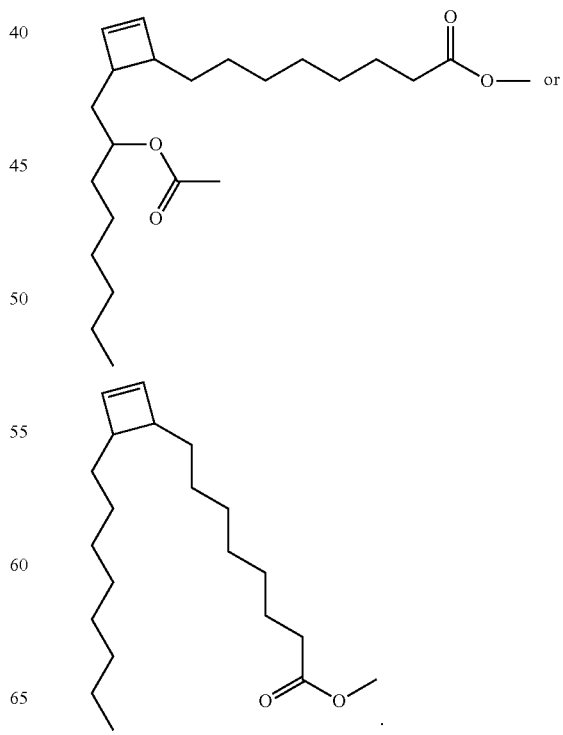

In some embodiments, at least one of $R^3$ or $R^4$ is a $C_1$-$C_{40}$ alkyl. For example, if $R^4$ is H, then $R^3$ is a $C_1$-$C_{40}$ alkyl (e.g., $C_5$-$C_{20}$ alkyl, $C_{10}$-$C_{30}$ alkyl, and $C_2$-$C_8$ alkyl), or if $R^3$ is absent, then $R^4$ is $C_1$-$C_{40}$ alkyl (e.g., $C_5$-$C_{20}$ alkyl, $C_{10}$-$C_{30}$ alkyl, and $C_2$-$C_8$ alkyl). In some embodiments, $R^3$ is a $C_1$-$C_{10}$ alkyl. In some embodiments, $R^3$ is a $C_1$-$C_{10}$ alkyl. For example, $R^3$ can be a $C_7$ alkyl. In some embodiments, $R^4$ is a $C_1$-$C_{10}$ alkyl. For example, $R^4$ can be a $C_8$ alkyl. In some embodiments, $R^4$ is H. $R^3$ and $R^4$ can be independently optionally substituted. For example, substituents include, but are not limited to, $Cy^1$, $C_{1-6}$ alkyl, $C_{2-6}$ alkenyl, $C_{2-6}$ alkynyl, halo, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$;

each $Cy^1$ is independently $C_{6-10}$ aryl, $C_{3-10}$ carbocyclyl, 5-10 membered heteroaryl or 4-10 membered heterocyclyl, each of which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$; $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$ and oxo;

each $R^{a1}$, $R^{b1}$, $R^{c1}$, $R^{d1}$, is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ carbocyclyl, 5-10 membered heteroaryl, 4-10 membered heterocyclyl, $C_{6-10}$ aryl-$C_{1-4}$ alkyl, $C_{3-10}$ carbocyclyl-$C_{1-4}$ alkyl, (5-10 membered heteroaryl)-$C_{1-4}$ alkyl or (4-10 membered heterocyclyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ carbocyclyl, 5-10 membered heteroaryl, 4-10 membered heterocyclyl, $C_{6-10}$ aryl-$C_{1-4}$ alkyl, $C_{3-10}$ carbocyclyl-$C_{1-4}$ alkyl, (5-10 membered heteroaryl)-$C_{1-4}$ alkyl and (4-10 membered heterocyclyl)-$C_{1-4}$ alkyl is optionally substituted with 1, 2, 3, 4, or 5 substituents independently selected from $C_{1-4}$ alkyl, $C_{1-4}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$ and $S(O)_2NR^{c4}R^{d4}$;

each $R^{a4}$, $R^{b4}$, $R^{c4}$ and $R^{d4}$ is independently selected from H, $C_{1-4}$ alkyl, $C_{1-4}$ haloalkyl, $C_{2-4}$ alkenyl and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy.

In some embodiments, the substituents can be selected from the group consisting of an alkyl, a halogen, a hydroxyl, an alkoxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a carbocyclyl, a heterocyclyl, an aralkyl, a heteroaralkyl, or an aromatic or heteroaromatic moiety.

In some embodiments, the hydrocarbon backbone formed by $R^3$ and $R^4$ is a fatty acid or a derivative thereof which contains a cyclobutene moiety. In some embodiments, $R^3$ and $R^4$ together with the cyclobutene moiety form a hydrocarbon chain with a reactive group at one terminus (e.g., carboxylic acid or a Z moiety as defined above). In some embodiments, the hydrocarbon chain ranges from 10 to 30 carbon atoms and may be substituted or unsubstituted. Non-limiting examples include myristoleic acid, pamitoleic acid, sapienic acid, oleic acid, linoleic acid, linolenic acid, arachadonic acid, elaidic acid, and vaccenic acid.

In some embodiments, Z is $CO_2R^6$.

As noted above, any known method of polymerization for alkenes may be used with the monomers described herein. For example, in the presence of selected transition metal catalysts, a monomer as provided herein can undergo metathesis with other alkenes. In the absence of a thermodynamic driving force, these exchange reactions typically produce mixtures of the starting and product alkenes. For the monomers provided herein, however, the metathesis reaction is driven forward by relief of strain to result in rapid and typically irreversible ring-opening metathesis polymerization (ROMP). As shown in Scheme 2 for a ROMP process with a generic cycloalkane.

Scheme 2

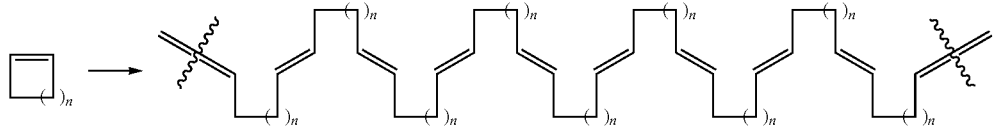

See, for example, Bielawski, Christopher W.; and Grubbs, Robert H., *Progress in Polymer Science* (2007), 32(1), 1-29. Publisher: Elsevier Ltd.; Trimmel, Gregor, et al. *Advances in Polymer Science* (2005), 176(Metathesis Polymerization), 43-87. Publisher: Springer GmbH; Slugovc, Christian, *Macromolecular Rapid Communications* (2004), 25(14), 1283-1297; Grubbs, Robert H. and Khosravi, Ezat. *Materials Science and Technology* (1999), 20 (Synthesis of Polymers), 65-104 Publisher: Wiley-VCH; Buchmeiser, Michael R. *Chemical Reviews* (Washington, D.C.) (2000), 100(4), 1565-1604; Madan, Rajni, et al., *Progress in Polymer Science* (1998), 23(4), 621-663.

With a monomer as provided herein, an example reaction is as shown in Scheme 3.

Scheme 3

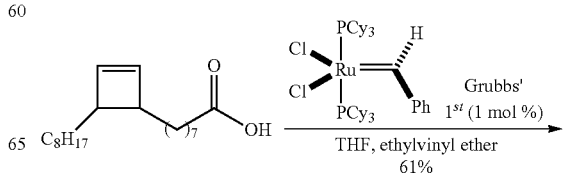

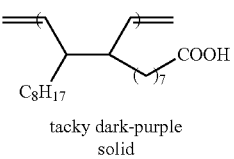

tacky dark-purple solid

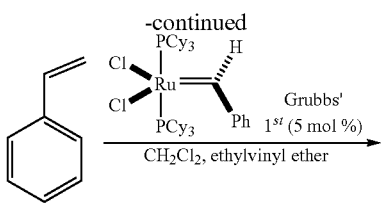

In some embodiments, one or more monomers as provided herein can be reacted with other alkenes, either monomeric alkenes or alkene-containing polymers, through cross metathesis (CM) wherein two alkenes can undergo transalkylidenation under release of ethane in the presence of a ruthenium carbenoid (e.g., Grubbs' Catalyst). In the absence of a thermodynamic driving force, these exchange reactions typically produce mixtures of the starting and product alkenes. For the cyclobutene-containing monomers provided herein, however, the cross metathesis reaction is driven forward by relief of strain. Two exemplary reactions with monomeric alkenes are shown in Scheme 4.

Scheme 4

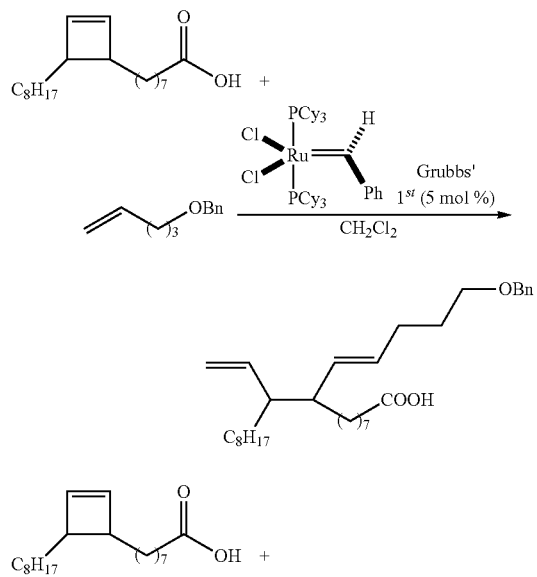

For example, a polymer can be prepared as follows. Under an inert atmosphere, a solution of catalyst (Grubbs' I or II) in THF was added to a vigorously stirred solution of 0.2 M monomer in THF. The reaction mixture is then stirred for about 30 min at room temperature after which the reaction is terminated by addition of a small amount of ethyl vinyl ether. The mixture is allowed to stir at room temperature for 30 min. and poured into methanol to precipitate the polymer. The polymer is then resolubilized in dry THF and the solutions dried with typical agents (magnesium sulfate, sodium sulfate) before further purification reprecipitation using dry methanol (2×). The polymer can be analyzed by gel permeation chromatography (GPC) in THF or by proton $^1$H NMR as a solution in $CDCl_3$.

In some embodiments, radical polymerization methods may be used to prepare a polymer as provided herein. Free radical polymerization is a method of polymerization by which a polymer forms by the successive addition of free radical building blocks. Free radicals can be formed via a number of different mechanisms usually involving separate initiator molecules. Following its generation, the initiating free radical adds (nonradical) monomer units, thereby growing the polymer chain. Any reasonable initiator may be used in these polymerization reactions. An example of such a reaction is shown in Scheme 5.

Scheme 5

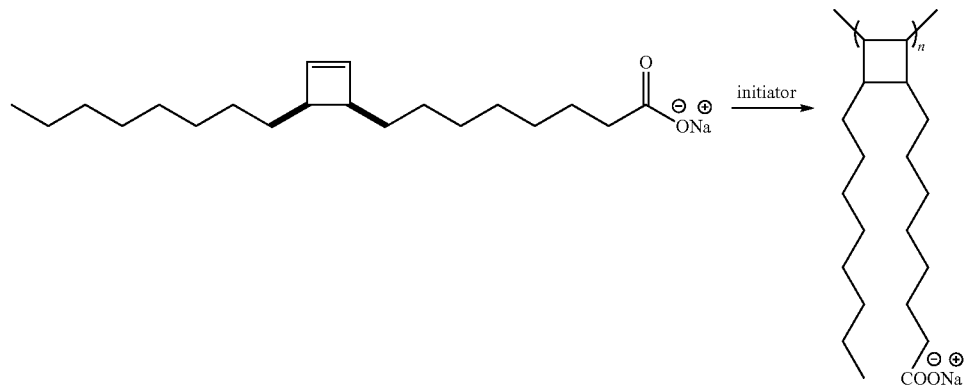

The cyclobutene compounds provided herein are also useful in bioorthogonal "click" chemistries. Bioorthogonal reactions for coupling materials in the presence of complex biological milieu are of great interest in biology and medicine. Such reactions have become key components in a variety of applications including protein engineering, immunoassay development, and cell surface modification. (Link J A et al., 2003, Curr Opin Biotechnol 14:603-609; Wang Q et al., 2003, J Am Chem Soc 12:3192-3193; Dimandis E P et al., 1991, Clin Chem 37:625-636; Baskin J M et al., 2007, Proc Natl Acad Sc. USA 104:16793-16797; Link J A et al., 2003, J Am Chem Soc 125:11164-11165). Presently, a few types of bioorthogonal reactions have been reported, the most popular being the Staudinger ligation and the [3+2] cycloaddition "click" reaction between azides and alkynes. (Prescher J A et al., 2004, Nature 430(7002):873-877; Rostovtsev V V et al., 2002, Angew Chem Int Ed 41(14): 2596-2599).

Bioorthogonal "click" chemistries are widely used in chemical biology for a myriad of applications such as activity based protein profiling, crosslinking of proteins, monitoring cell proliferation, generation of novel enzyme inhibitors, monitoring the synthesis of newly formed proteins, protein target identification, and studying glycan processing. Perhaps the most fascinating applications involve using these bioorthogonal chemistries to assemble molecules in the presence of living systems such as live cells or even whole organisms (Baskin et al., 2007, Proc Natl Acad Sci USA, 104, 16793-7; Laughlin et al., 2008, Science, 320, 664-7; Prescher and Bertozzi, 2005, Nat Chem Biol, 1, 13-21; Neef and Schultz, 2009, Angew Chem Int Ed Engl, 48, 1498-500; Ning et al., 2008, Angewandte Chemie-International Edition, 47, 2253-2255). These latter applications require that the chemistry be non-toxic and possess kinetics that allow fast reaction to occur with micromolar concentrations of reagents in a time span of minutes to hours.

Bioconjugation methods using inverse electron demand Diels-Alder cycloadditions between tetrazines and highly strained dienophiles such as norbornene and trans-cyclooctene are known in the literature, however the tetrazine used has limited stability to aqueous media. (Blackman et al., 2008, J Am Chem Soc, 130, 13518-9; Devaraj et al., 2009, Angew Chem Int Ed Engl, 48, 7013-6; Devaraj et al., 2008, Bioconjug Chem, 19, 2297-9; Pipkom et al., 2009, J Pept Sci, 15, 235-41). To improve upon the stability of the tetrazine, a novel asymmetric tetrazine was employed that demonstrated superior stability in water and serum and can react with trans-cyclooctene at rates of approximately $10^3$ $M^{-1}$ $sec^{-1}$ at 37° C. (Devaraj et al., 2009, Angew Chem Int Ed Engl, 48, 7013-6). This extremely fast rate constant allows for the labeling of extracellular targets at low nanomolar concentrations of tetrazine labeling agent, concentrations that are sufficiently low to allow for real-time imaging of probe accummulation.

In some embodiments, the ligand, e.g., an antibody, small molecule or other biomolecule, can be physically attached to the dienophile. In some embodiments, the ligand carries a functional group such as an amine, alcohol, carboxylic acid or ester, or other group of atoms on the ligand that can undergo a chemical reaction allowing attachment to the dienophile. Alternatively or in addition, the dienophile or heterodienophile (e.g., a cyclobutene compound as provided herein) possesses a reactive functional group for attachment to the ligand (e.g., Z). Thus, the reactive functional group on the ligand and/or dienophile undergoes a chemical reaction to form a link between the two.

In some embodiments, the diene can be a substituted tetrazine or other heteroaromatic ring system with at least two nitrogens adjacent to each other and which is a highly reactive participant in the inverse electron demand Diels-Alder reaction. The diene is linked to the payload (which can be, e.g., a therapeutic agent, fluorescence dye, or other detectable agent). In these embodiments, the diene possesses a reactive group such as an amine, alcohol, carboxylic acid or ester, or other group that can undergo a chemical reaction with the reactive moiety on the payload to form a link between the two.

Dienes

Dienes useful in the present disclosure include but are not limited to aromatic ring systems that contain two adjacent nitrogen atoms, for example, tetrazines, pyridazines, substituted or unsubstituted 1,2-diazines. Other 1,2-diazines can include 1,2-diazines annelated to a second n-electron-deficient aromatic ring such as pyrido[3,4-d]pyridazines, pyridazino[4,5-d]pyridazines, and 1,2,4-triazines. Pyridazines can also be fused with a five-membered heterocycle such as imidazo[4,5-d]pyridazines and 1,2,3-triazolo[4,5-d]pyridazines. In some preferred embodiments, the diene is an asymmetrical tetrazine as described herein, e.g., 3-(p-Benzylamino)-1,2,4,5-tetrazine:

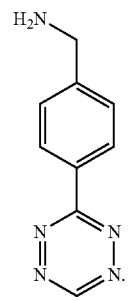

Two non-limiting examples of such a "click" chemistry reaction is shown in Scheme 6.

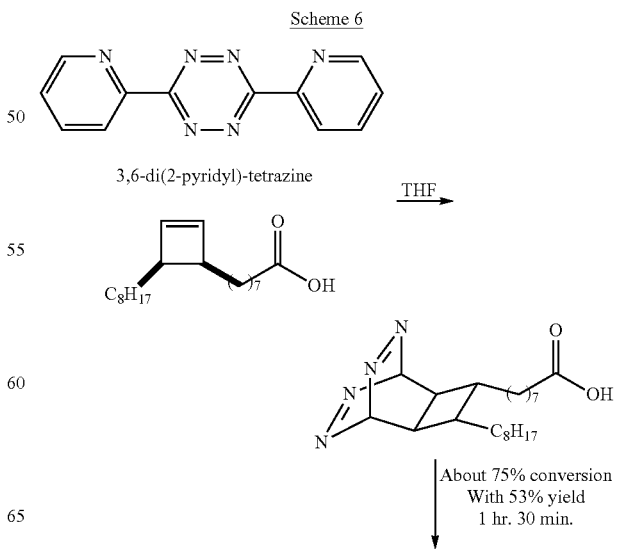

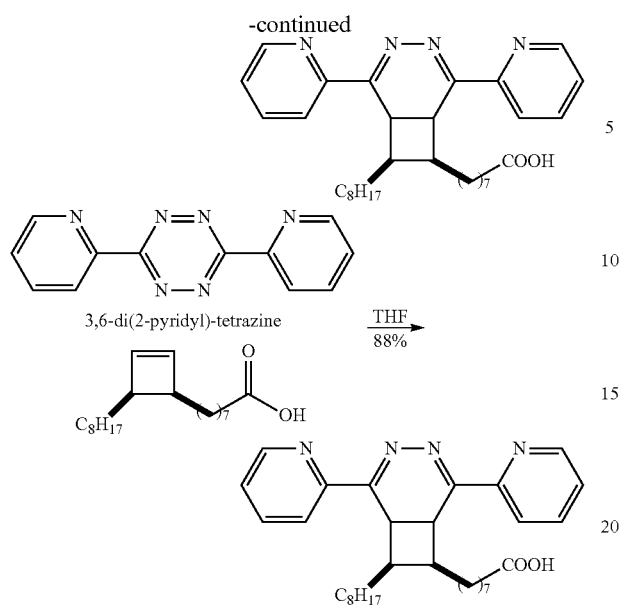

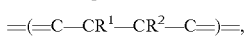

Accordingly, provided herein is an amphiphilic polymer formed by polymerizing a compound as provided herein (e.g., a compound of Formula (IV) or an amphiphilic cycloalkene-containing fatty acid derivative), each having a hydrophobic end, a hydrophilic end, and a backbone there between comprising a cycloalkene, wherein the cycloalkene comprises at least four carbon atoms, with at least two of the four carbon atoms being part of the backbone of the amphiphilic cycloalkene-containing fatty acid derivatives. In some embodiments, the polymer comprises amphiphilic fatty acid derivatives cross-linked via an unsaturated hydrocarbon chain formed by cleavage of the cycloalkene. In some embodiments, the polymer is ordered in two or three dimensions.

Further provided herein is a polymer comprising a repeating unit having the structure

=(=C—CR$^1$—CR$^2$—C=)=, where:
R$^1$ is hydrophobic and comprises a substituted or unsubstituted alkyl group having at least one carbon atom or a substituted or unsubstituted alkenyl group having at least two carbon atoms, and
R$^2$ is hydrophilic and comprises a substituted alkyl group having at least one carbon atom or a substituted alkenyl group having at least two carbon atoms.

In some embodiments, the substituted alkyl group or substituted alkenyl group of R$_2$ comprises a hydroxyl group, an ester group, an aldehyde group, a carboxyl group, a sulfhydryl group, an amine group, an amide group, a carbamide group, or a phosphate group.

The polymers provided herein may be used in a number of applications. For example, the polymers may undergo further manipulation such as cleavage, stabilization, and/or cross-linking. For example, the carbon-carbon double bonds introduced through certain polymerization reactions (e.g., ROMP polymerization) can be cleaved by oxone or a similar oxidant, thus providing a means of breaking the polymer back to monomeric components. In some cases, the carbon-carbon double bonds which provide the cross-linking element can be saturated (hydrogenated) to form highly stable alkane linkages, making the polymer much less susceptible to oxidative cleavage. In some embodiments, the carbon-carbon double bonds which provide the cross-linking element can be cross-linked by the same methods used for latex of butadiene rubbers, allowing the incorporation of a two-dimensional crosslink within a coating or layer.

The polymers provided herein can form two-dimensional or three-dimensional ordered polymers or coatings. For example, see Scheme 7.

Scheme 7

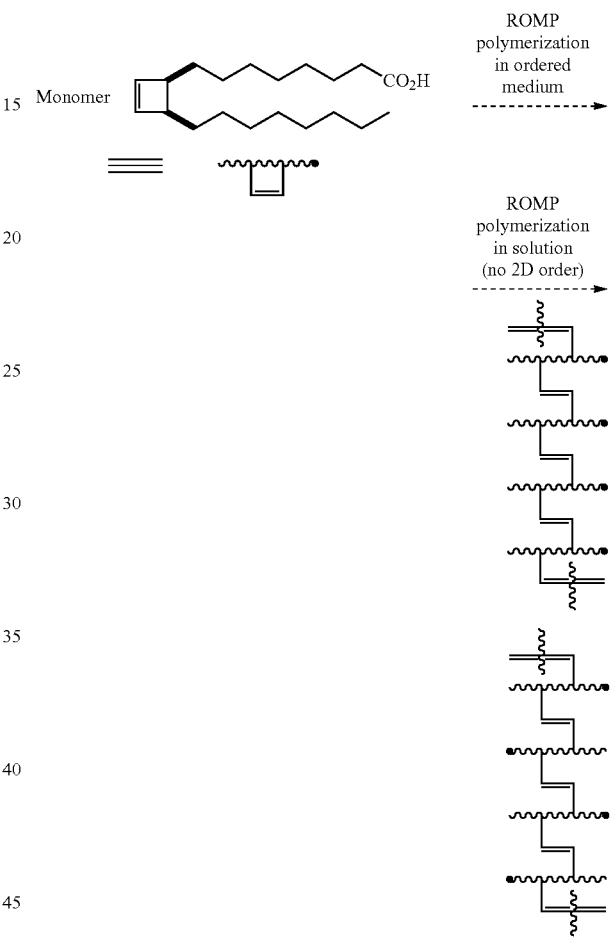

Examples of applications of such polymers or coatings include:
1) Polymerization of monolayer or multilayer films derived from Langmuir-Blodgett techniques (either directly on a Langmuir trough or after transfer of a monolayer or multi layers to a substrate by dipping).
2) Polymerization of monolayer or multilayer films derived from polar interactions between the amphiphile and inorganic or organometallic colloids such as quantum dots.
3) Polymerization within micelles, bilayers, liquid crystals, and liposomes. These aggregates may be composed solely of the amphiphilic cyclobutenes or else mixtures of the amphiphilic cyclobutenes with other amphiphilic components.
4) Polymerization of monolayer or multilayer films of the amphiphilic cyclobutenes onto a chromatographic support such as silica to create a remarkably stable reverse-phase chromatographic layer capable of displaying any desired functional group that can be incorporated into the cyclobutene precursors. By way of comparison, commercial reverse phase chromatography columns are prepared by chemical bonding of C8 or C18 alkylsilanes to a silica surface via siloxane bonds. The resulting siloxanes are only stable within a fairly modest pH range. If a reverse-phase chromatography column was instead prepared using a cyclobutene-substituted monomer (for example, with a terminal siloxane grafted onto or in place of the carboxylic acid), treatment with a ROMP catalyst could provide a new chromatographic support maintaining the same fundamental features of existing supports yet possessing far greater hydrolytic stability.

5) The ability to prepare cyclobutenes having a close structural analogy to natural fatty acids, combined with the facility of achieving cross-metathesis of the cyclobutenes with other alkenes, will enable the use of the cyclobutene fatty acid as a means of stabilizing or solubilizing proteins or chemical reagents within biological membranes. A targeted protein or agent would be functionalized with one or more alkene units (in the form of allyl ethers, allyl esters, or allyl amides) and then subjected with cross-metathesis with a cyclobutene fatty acid to create a protein "decorated" with fatty acids, fatty acid esters, phospholipids, or triglycerides.

6) Polymerization or cross-metathesis of cyclobutene-containing fatty acids, or their conjugates with proteins, after absorption within the skin, hair, or nail, would result in a new class of remarkably durable cosmetic and therapeutic agents. The ability to polymerize the absorbed fatty acid under conditions that selectively target the cyclobutene would create strong and biomimetic coatings, with potential applications for cosmetics, skin protective or tanning agents, hair thickeners, and wound coatings.

Synthesis

The compounds provided herein, including salts thereof, can be prepared using known organic synthesis techniques and can be synthesized according to any of numerous possible synthetic routes.

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry*, 1$^{st}$ Ed., Oxford University Press, 2000; *March's Advanced Organic Chemistry: Reactions, Mechanisms, and Structure*, 5$^{th}$ Ed., Wiley-Interscience Publication, 2001; and Peturssion, S. et al., "*Protecting Groups in Carbohydrate Chemistry,*" *J Chem. Educ.*, 74(11), 1297 (1997).

Reactions can be monitored according to any suitable method known in the art. For example, product formation can be monitored by spectroscopic means, such as nuclear magnetic resonance spectroscopy (e.g., $^{1}$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6), 874 (2004) and normal phase silica chromatography.

In some embodiments, the compounds provided herein can be prepared as described in the Examples provided herein and as illustrated in Scheme 8:

Scheme 8

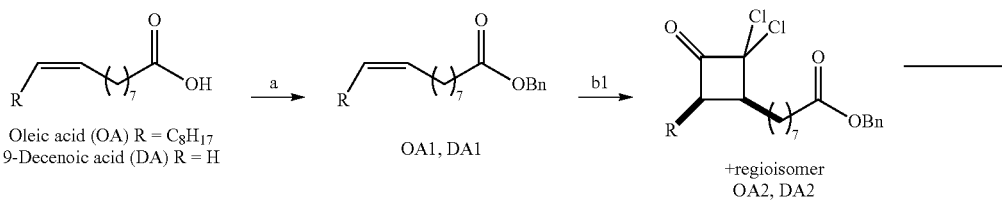

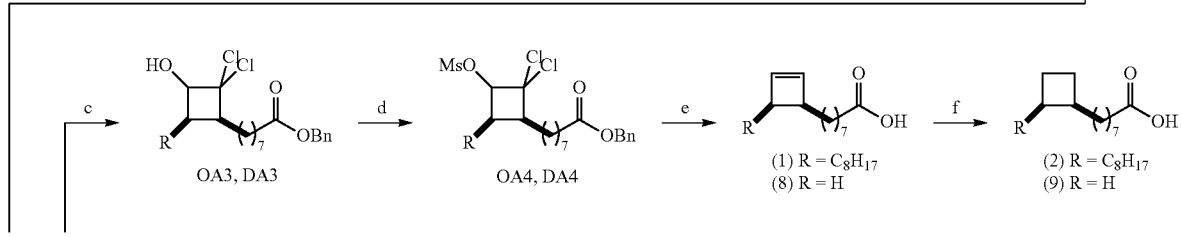

-continued

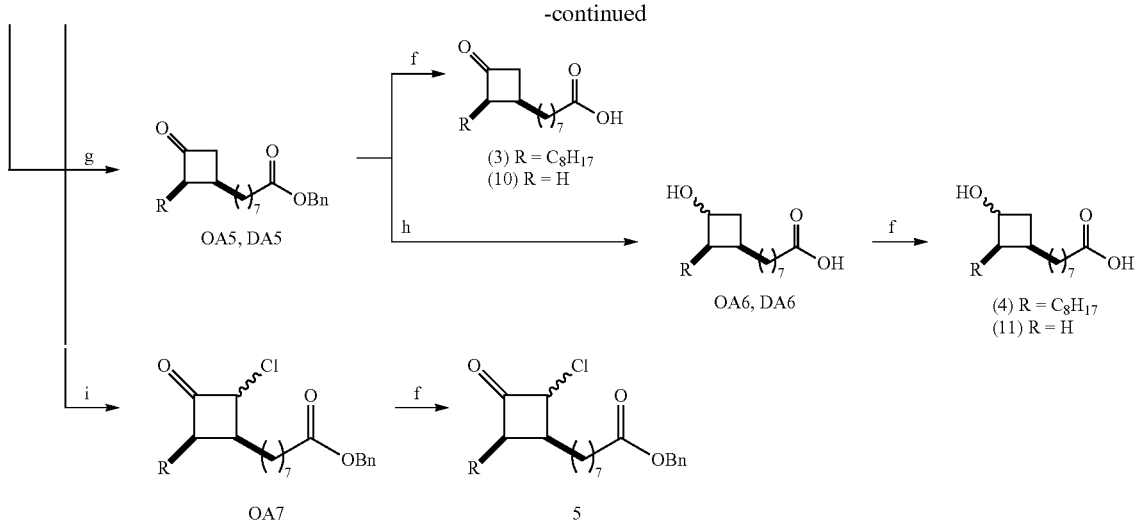

a) DMAP, DCC, BnOH, 85% (OA1), 99% (DA1); b1) Zn dust (5 equiv), Cl$_3$CCOCl (2.5 equiv) rt, ether, 85% for OA2 and 80% for DA2; b2) Zn(Cu) (5 equiv), Cl$_3$CCOCl (2.5 equiv), rt, ether 63%; c) NaBH$_4$, 2-propanol, 55% (OA3), 57% (DA3); d) MsCl, Et$_3$N, 92% (OA4 and DA4); e) Na/NH$_3$, -78 to -33° C., 87% (1), 52% (8); f) H$_2$, Pd/C EtOAc, 96% (2), 89% (9), 87% (3), 90% (10), 81% (4), 54% (11), 70% (5); g) Zn (5 equiv), AcOH 87% (OA5) and 59% (DA1); h) NaBH$_4$, MeOH, -10° C., 99% for OA6 and 76% for DA6; i) Zn, (1.1 equiv), AcOH, 97% for OA5 and 70% for EA5.

As shown above, the preparation of cyclobutene compounds as provided herein (e.g., 1) can occur using the following procedures. The benzyl ester of oleic acid undergoes cycloaddition with dichloroketene to afford a mixture of regioisomeric dichlorocyclobutanones, each predominantly as the cis stereoisomer. The dichlorocyclobutanones possessed limited stability and are directly reduced with sodium borohydride to furnish a mixture of regioisomeric 2,2-dichloro-1-cyclobutanols. Conversion to the corresponding methanesulfonate (mesylate) esters is followed by reaction with sodium in ammonia, resulting in simultaneous deprotection of the benzyl ester and fragmentation/reduction of the β-chloromethanesulfonate, generating cyclobutene 1 in quantities of up to several hundred milligrams. Hydrogenation of the compound can provide the corresponding cyclobutane (e.g., 2). A cyclobutanone (e.g., 3) and cyclobutanol (e.g., 4) analogs can be prepared through a variation of the above in which the initial dichlorocyclobutanone is dehalogenated, for example, with excess zinc in acetic acid. A mixture of regioisomeric monochlorocyclobutanones (e.g., 5) can be prepared by partial reduction of the dichlorocyclobutanone with 1.1 equiv of Zn or Zn(Cu) in acetic acid. For the preparation of cyclobutanone, cyclobutanol and monochlorocyclobutanones, the final step can include removal of the benzyl ester by Pd-mediated hydrogenolysis.

Compound having shorter chains (e.g., 8-11) can be prepared analogously from 9-decenoic acid, furnishing comparably functionalized substrates with lower log P. The trans-stereoisomers of cyclobutenes (e.g., 2) and monochlorocyclobutanones (e.g., 7) can be prepared using a similar route based upon elaidic acid (Scheme 9). In some cases, the cycloaddition step can be conducted only in the presence of activated Zn or Zn/Cu.

Scheme 9

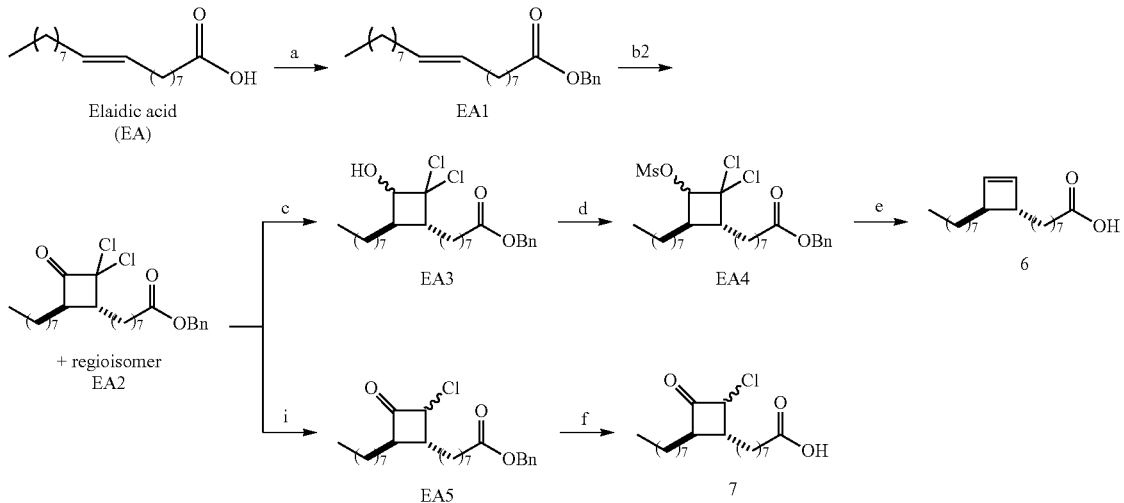

a) DMAP, DCC, BnOH, 95% (EA1); b2) Zn(Cu) (5 equiv), Cl$_3$CCOCl (2.5 equiv), rt, ether 63%; c) NaBH$_4$, 2-propanol, 85% (EA3); d) MsCl, Et$_3$N, 86% (EA4); e) Na/NH$_3$, -78 to -33° C., 46% (6); f) H$_2$, Pd/C EtOAc, 54% (7).

Accordingly, provided herein is a method comprising:
reacting an unsaturated fatty acid or derivative thereof having a backbone comprising at least one carbon-carbon double bond with dihaloketene (e.g., dichloroketene or dibromoketene) to achieve a stereospecific cycloaddition across the at least one carbon-carbon double bond, thereby yielding a cycloketone-containing fatty acid derivative comprising a cycloketone along the backbone, wherein the cycloketone comprises at least four carbon atoms, with at least two of the at least four carbon atoms being part of the backbone of the cycloketone-containing fatty acid derivative;
reducing the cycloketone-containing fatty acid derivative to yield an amphiphilic cycloalkene-containing fatty acid derivative having a hydrophobic end, a hydrophilic end, and a backbone therebetween comprising a cycloalkene, wherein the cycloalkene comprises at least four carbon atoms, with at least two of the four carbon atoms being part of the backbone of the amphiphilic cycloalkene-containing fatty acid derivative.

In some embodiments, the method further comprises polymerizing a multiplicity of the amphiphilic cycloalkene-containing fatty acid derivatives to yield a polymer comprising carbon-carbon double bonds. In some such embodiments, polymerization can include cross-linking the amphiphilic cycloalkene-containing fatty acid derivatives via the carbon-carbon double bond in the cycloalkene. In some embodiments, polymerizing the multiplicity of the amphiphilic cycloalkene-containing fatty acid derivatives comprises ring-opening metathesis reactions. In some embodiments, polymerizing the multiplicity of the amphiphilic cycloalkane-containing fatty acid derivatives comprises click-chemistry. For example, the amphiphilic cycloalkane-containing fatty acid derivative can be reacted with a substituted or unsubstituted tetrazine.

In some embodiments, the method further comprises hydrogenating the carbon-carbon double bonds of the polymer. In some embodiments, the method further comprises cleaving at least some of the carbon-carbon double bonds in the polymer via oxidation to yield monomeric products.

The backbones of the multiplicity of the amphiphilic cycloalkene-containing fatty acid derivatives can be aligned before polymerizing the multiplicity of the amphiphilic cycloalkene-containing fatty acid derivatives.

EXAMPLES

The invention is further described in the following examples, which do not limit the scope of the invention described in the claims.

General Procedures

All reagents and solvents were used as purchased except for pyridine and $CH_2Cl_2$ (distilled from $CaH_2$ and kept under $N_2$) and THF (distilled from Na/benzophenone under $N_2$). Thin-layer chromatography (TLC) was performed on 0.25 mm hard-layer silica G plates; developed plates were visualized with a hand-held UV lamp or by staining: 1% $Ce(SO_4)_2$ and 10% $(NH_4)_2MoO_4$ in 10% aq. $H_2SO_4$ (general stain, after heating); 1% aq. $KMnO_4$ (for unsaturated compounds); 3% vanillin in 3% $H_2SO_4$ in EtOH (general stain, after heating). Unless otherwise noted, NMR (spectra were recorded at 400 MHz ($^1H$) or 100 MHz ($^{13}C$) in $CDCl_3$; peaks are reported as: chemical shift (multiplicity, J couplings in Hz, number of protons); "app" and "br" refer to apparent and broad signals, respectively. IR spectra were recorded as neat films (ZnSe, ATR mode) with selected absorbances reported in wavenumbers ($cm^{-1}$). Flash chromatography was performed on 32-60 μm silica gel. Preparative HPLC was performed on a 21×250 mm normal phase Si (8 micron) column at 10 mL/min of the indicated solvent unless otherwise noted. Analytical purity of compounds was checked using an analytical column (250 mm×4.6 mm; Microsorb) at 1 mL/min of 20% EtOAc/Hexane; detection was accomplished using a differential refractometer interfaced with a data module. All compounds tested for biological activity showed >97% purity by HPLC analysis except for 5 and 7. Melting points are uncorrected. Mass spectral analyses were carried out by HRFAB on 3-nitrobenzyl alcohol (3-NBA) or glycerol matrices at the Nebraska Center for Mass Spectrometry.

Example 1—Preparation of Compounds (Z)-9-Octadecenoate, benzyl ester (benzyl oleate, OA1) was prepared by a variation of a known procedure (Raviglione, M. et al. *Lancet* 2012, 379: 1902-1913). Benzyl alcohol (3.83 g, 35.4 mmol) was added to a stirred solution of oleic acid (5.136 g, 18.1 mmol) and DMAP (43.7 mg, 3.57 mmol) in $CH_2Cl_2$ (40 mL). The solution was cooled to 0° C. and DCC (4.211 g, 20.4 mmol) was added. The mixture was allowed to warm to room temperature and was stirred for 2.5 hours. The resulting suspension was filtered through a cotton plug and the precipitate was washed with $CH_2Cl_2$. The $CH_2Cl_2$ solution was washed with water and dried over $Na_2SO_4$. Evaporation of the organic solvent and flash chromatography of the residue over silica gel, using 5% EtOAc/Hex, gave benzyl oleate OA1 (5.73 g, 85%) as a colorless oil: $R_f$=0.83 (10% EtOAc/Hex); IR (ZnSe, $cm^{-1}$) 2924, 2853, 1738, 1456, 1162, 696 $cm^{-1}$; $^1H$ NMR: δ 7.38-7.31 (5H), 5.41-5.31 (2H), 5.13 (s, 2H), 2.37 (t, J=7.6 Hz, 2H), 2.05-2.00 (4H), 1.70-1.62 (m, 2H), 1.40-1.29 (20H), 0.90 (t, J=6.8 Hz, 3H); $^{13}C$ NMR δ 173.6, 136.12, 129.9, 129.7, 128.5 (two overlapping signals), 128.11, 128.09, 66.0, 34.3, 31.9, 29.7, 29.6, 29.50, 29.3, 29.1, 29.1, 27.2, 27.1, 24.9, 22.7, 14.1.

2,2-Dichloro-4-(octanoic acid benzyl ester, 8-yl) 3-octylcyclobutanone-; 2,2-Dichloro-3-(octanoic acid benzyl ester, 8-yl) 4-octylcyclobutanone (OA2); was prepared by a modification of a known procedure (Raviglione, M. et al. *Lancet* 2012, 379: 1902-1913). To a mixture of zinc dust (0.879 g, 13.4 mmol) and benzyl oleate OA1 (1.019 g, 2.73 mmol) in 20 mL of anhydrous ether was slowly added a solution of trichloroacetyl chloride (0.75 mL, 6.8 mmol) in 7 mL of diethyl ether via dropping funnel over a period of 45 min. The reaction was stirred until judged complete by the absence of starting material (4 h, TLC). The reaction mixture was filtered through a plug of Celite and the residue was washed with ether (2×75 mL). The organic solution was stirred a minimum with 50% aq. $NaHCO_3$ and the separated aqueous layer back-extracted with ether (2×20 mL). The combined organic layers were dried over $Na_2SO_4$ and concentrated under vacuum to give 1.3041 g of the product (99%) as a yellow oil. The unpurified material was generally used directly for the next reaction because of a tendency to decompose during chromatography. However, small quantities could be purified by rapid flash chromatography (5% EtOAc/Hex) to afford a 1:1 mixture of regioisomeric dichlorocyclobutanones OA2 as a colorless oil: $R_f$=0.53 (10% EtOAc/Hex); IR (ZnSe, $cm^{-1}$) 2926, 2855, 1800, 1735, 1456, 1162, 696 $cm^{-1}$; $^1H$ NMR: δ 7.36-7.32 (5H), 5.120/5.116 (overlapping s, 2H), 3.55-3.49 (m, 1H) 2.97-2.93 (m, 1H), 2.37/2.35 (overlapping t, J=7.6 Hz, 2H), 1.74-1.62 (m, 4H), 1.66-1.48 (m, 4H), 1.45-1.27 (br m, 18H), 0.89/0.88 (overlapping triplets, J=6.9 Hz, total 3H); $^{13}C$ NMR δ 197.5, 173.5, 136.1, 128.5, 128.1, 88.1, 66.0, 58.0, 57.9, 49.4, 49.4, 34.2, 31.8, 31.80, 29.60, 29.3, 29.3, 29.2, 29.18, 29.15, 29.12, 29.0, 28.9, 28.9, 28.04, 27.96, 26.72, 26.68, 26.3; HRFAB-MS (3-NBA+Li matrix): calcd. for $C_{27}H_{40}O_3Cl_2Li$ [M+Li]$^+$:489.2515. Found: 489.2499.

2,2-Dichloro-4-(octanoic acid benzyl ester, 8-yl) 3-octylcyclobutanol-; 2,2-Dichloro-3-(octanoic acid benzyl ester, 8-yl) 4-octylcyclobutanol (OA3). Reduction of the dichlorocylobutanone OA2 was achieved using a known procedure (Raviglione, M. et al. Lancet 2012, 379: 1902-1913). To a 0° C. solution of the mixture of regioisomeric dichlorocyclobutanones OA2 (1.5 g, 3.1 mmol) in iPrOH (45 mL) was added NaBH$_4$ (0.176 g, 4.65 mmol). The reaction was allowed to slowly warm to rt and stirred only until the starting material had disappeared (TLC, ~2.5 h; byproducts tended to accumulate upon prolonged reaction). The reaction was then cooled to 0° C. and quenched with 1N HCl (40 ml). The solution was stirred for an additional 30 min and then extracted with EtOAc (3×100 mL). The organic layer was washed sequentially with water/sat. NaHCO$_3$/brine and then dried over Na$_2$SO$_4$. Evaporation of the organic solvent and flash chromatography of the residue on silica gel, using a step gradient of 5%/10% EtOAc/Hex, gave 0.8212 g (55% yield) of a 1:1 mixture of regioisomeric cyclobutanols S2 as a colorless oil. The products were predominantly a regioisomeric mixture of the cis, cis diastereomers based on $^1$H NMR, HSQC, 2D-COSY and 2D-NOESY analysis: R$_f$(10% EtOAc/Hex)=0.33 (major, OH is cis to backbone) 0.28 (minor, OH is trans to backbone), 0.2 (major, OH is cis to backbone) and 0.15 (minor, OH is trans to backbone); IR (ZnSe, cm$^{-1}$) 3473, 3036, 2924, 2854, 1733, 1456, 1168, 696 cm$^{-1}$; $^1$H NMR: δ 7.36-7.32 (m, 5H), 5.116/5.112 (app s, total 2H), 4.55 (dd, J=10.8, 8.8 Hz, 0.92H, CH—OH, cis to the backbone assigned based on 2D-NOESY analysis and $^4J_{diagonal\ H}$=0), 3.99 (br t, J=10 Hz, 0.08H), 2.75-2.69 (m, 1H), 2.64/2.62 (overlapping d, J=10.8 Hz, total 1H, —H proton assigned based on the disappearance of this peak upon D$_2$O addition), 2.60-2.55 (m, 1H), 2.36/2.35 (overlapping t, J=7.6 Hz, total 2H), 1.67-1.62 (bm, 3H), 1.52-1.19 (24H), 0.89/0.88 (overlapping t, J=6.8 Hz, total 3H). Small quantities of the individual isomers could be isolated by semipreparative HPLC (10% EtOAc/Hex, RI detection):

first-eluting cis: R$_f$=0.33; IR (ZnSe, cm$^{-1}$) 3457, 2924, 2854, 1736, 1456, 1170, 697 cm$^{-1}$; $^1$H NMR: δ 7.37-7.32 (m, 5H), 5.12 (s, 2H), 4.55 (dd, J=10.8, 8.8 Hz, 1H, CH—OH, cis to the backbone assigned based on 2D-NOESY analysis and $^4J_{diagonal\ H}$=0), 2.72 (dt, J=9.2, 5.6 Hz, 1H), 2.59 (d, J=10.8 Hz, 1H, —OH), 2.55 (app dq, J=9.2, 5.6 Hz, 1H), 2.36 (t, J=7.6 Hz, 2H), 1.67-1.51 (br m, 3H), 1.52-1.13 (m, 24H), 0.88 (app t, J=6.8 Hz, 3H); $^{13}$C NMR δ 173.6, 136.1, 128.5 (two overlapping signals), 128.2 (two overlapping signals), 93.5, 77.2, 66.1, 49.5, 40.9, 34.3, 31.8, 29.9, 29.4, 29.4, 29.3, 29.2, 29.0, 27.0, 25.7, 24.9, 23.2, 22.7, 14.1; HRFAB-MS (3-NBA matrix): calcd. for $C_{27}H_{43}O_3Cl_2$:485.2589 [M+H]$^+$. Found: 485.2572.

first-eluting trans: R$_f$=0.28; IR (ZnSe, cm$^{-1}$) 3449, 3028, 2920, 2850, 1736, 1456, 1157, 696 cm$^{-1}$; $^1$H NMR: δ 7.37-7.32 (5H), 5.12 (s, 2H), 3.99 (ddd, J=10.0, 8.4, 1.2 Hz, 1H, CH—OH, trans to the backbone assigned based on 2D-NOESY analysis and $^4J_{diagonal\ H}$=1.2 Hz), 2.68-2.64 (m, 1H), 2.52 (d, J=10.0 Hz, 1H, —OH), 2.34 (t, J=7.6 Hz, 1H), 2.29-2.20 (m, 1H), 1.67-1.26 (br m, 27H), 0.88 (app t, J=6.8 Hz, 3H); $^{13}$C NMR δ 173.6, 136.1, 128.5 (two overlapping signals), 128.2 (two overlapping signals), 91.1, 82.6, 66.1, 50.3, 44.4, 34.3, 31.9, 29.7, 29.5, 29.2, 29.04, 28.4, 28.23, 28.15, 27.7, 24.9, 22.7, 14.1; ESI-MS: calcd. for $C_{27}H_{42}O_3Cl_2Na$: [M+Na]$^+$507.2409. Found: 507.2422.

Second-eluting cis: R$_f$=0.20; IR (ZnSe, cm$^{-1}$) 3464, 2924, 2854, 1736, 1456, 1169, 696 cm$^{-1}$; $^1$H NMR: δ 7.37-7.32 (m, 5H), 5.11 (s, 2H), 4.55 (dd, J=10.8, 8.8 Hz, 1HCH—OH, cis to the backbone assigned based on 2D-NOESY analysis and $^4J_{diagonal\ H}$=0), 2.72 (dt, J=9.2, 5.6 Hz, 1H), 2.65 (d, J=10.8 Hz, 1H, —OH), 2.54 (app dq, J=9.2, 5.6 Hz, 1H), 2.35 (t, J=7.2 Hz, 2H), 1.68-1.60 (bm, 3H), 1.52-1.13 (m, 24H), 0.89 (app t, J=6.8 Hz, 3H); $^{13}$C NMR δ 173.7, 136.1, 128.5 (two overlapping signals), 128.2 (two overlapping signals), 93.5, 77.2, 66.1, 49.5, 40.9, 34.3, 31.8, 29.6, 29.4, 29.2, 29.1, 29.04, 29.00, 27.0, 25.8, 24.8, 23.2, 22.7, 14.1; HRFAB-MS (3-NBA matrix): calcd. for $C_{27}H_{43}O_3Cl_2$: 485.2589 [M+H]$^+$. Found: 485.2581.

Second-eluting trans: R$_f$=0.15; IR (ZnSe, cm$^{-1}$) 3464, 3033, 2925, 2854, 1738, 1498, 1160, 697 cm$^{-1}$; $^1$H NMR: δ 7.37-7.32 (m, 5H), 5.11 (s, 2H), 3.99 (ddd, J=10.0, 8.4, 1.2 Hz, 1H, CH—OH, trans to the backbone assigned based on 2D-NOESY analysis and $^4J_{diagonal\ H}$=1.2 Hz), 2.69-2.64 (m, 1H), 2.56 (d, J=10.0 Hz, 1H, —OH), 2.35 (t, J=7.6 Hz, 2H), 2.26-2.22 (m, 1H), 1.66-1.26 (m, 27H), 0.88 (app t, J=6.8 Hz, 3H); $^{13}$C NMR δ 173.7, 136.1, 128.5 (two overlapping signals), 128.2 (two overlapping signals), 91.1, 82.6, 66.1, 50.3, 44.3, 34.3, 31.8, 29.7, 29.4, 29.2, 29.04, 28.97, 28.5, 28.21, 28.18, 27.5, 24.8, 22.7, 14.1; ESI-MS: calcd. for $C_{27}H_{42}O_3Cl_2Na$: [M+Na]$^+$507.2409. Found: 507.2426.

2,2-Dichloro-4-(octanoic acid benzyl ester, 8-yl) 3-octylcyclobutanol, methanesulfonate ester; 2,2-Dichloro-3-(octanoic acid benzyl ester, 8-yl) 4-octylcyclobutanol, methanesulfonate ester (OA4) was prepared by a variant of published procedures (see Baldwin, J. D. and Belfield, K. D. J. Org. Chem. 1987, 52, 4772-4776; and Powers, D. C. et al. J. Org. Chem. 2007, 72, 187-194): Methanesulfonyl chloride (62 μl, 0.80 mmol) was slowly added to a stirred 0° C. solution of a regioisomeric mixture of cyclobutanols OA3 (0.193 g, 0.398 mmol) and triethylamine (0.25 mL, 8 mmol) in CH$_2$Cl$_2$ (2 mL) over 15 min. The reaction was allowed to slowly warm to rt and was stirred for 17 h or until no starting material remained (TLC). The reaction was diluted with 75 inL of CH$_2$Cl$_2$ and washed sequentially with 1N HCl (2×25 mL), sat aq. NaHCO$_3$ (2×25 mL) and water (2×25 mL). The organic solution was then dried with Na$_2$SO$_4$ and concentrated under reduced pressure. The residue was purified by flash chromatography using 10% EtOAc/Hex to give a light yellow oil (0.2061 g, 92%) consisting of a 1:1 mixture of regioisomers, each a 92:8 mixture of cis/trans stereoisomers based upon $^1$H NMR: R$_f$(10% EtOAc/Hex)=0.31 (first trans), 0.26 (first cis/second trans), 0.21 (second cis); IR (ZnSe, cm$^{-1}$) 3032, 2925, 2855, 1735, 1458, 1180, 696 cm$^{-1}$; $^1$H NMR: δ 7.36-7.33 (m, 5H), 5.33 (d, J=9.6 Hz, 0.92H), 5.114/5.109 (two s, total 2H), 4.84 (d, J=7.6 Hz, 0.08H), 3.208/3.205 (two s, total 3H), 2.76-2.74 (m, 2H), 2.36/2.34 (two overlapping t, J=7.6 Hz, total 2H), 1.66-1.60 (m, 4H), 1.46-1.26 (m, 22H), 0.88/0.87 (overlapping t, J=6.8 Hz, total 3H).

Small quantities of individual isomers could be separated for analysis by HPLC using 10% EtOAc/Hex. The stereochemical assignments were confirmed by 2D-NMR experiments and by preparation of individual methanesulfonates from individual samples of alchols described in the previous step.

First eluting trans: R$_f$=0.31; IR (ZnSe, cm$^{-1}$) 3032, 2926, 2855, 1737, 1733, 1456, 1180, 697 cm$^{-1}$; $^1$H NMR: δ 7.37-7.32 (5H), 5.12 (s, 2H), 4.84 (d, J=7.6 Hz, 1H), 3.20 (s, 3H), 2.74-2.68 (m, 2H), 2.36 (t, J=7.6 Hz, 2H), 1.67-1.32 (br m, 26H), 0.88 (app t, J=6.8 Hz, 3H); $^{13}$C NMR δ 173.6, 136.1, 128.5 (two overlapping signals), 128.2 (two overlapping signals), 86.4, 85.8, 66.1, 50.5, 41.1, 39.5, 34.3, 31.8, 29.5, 29.4, 29.3, 29.2, 29.01, 28.98, 28.3, 28.1, 27.6, 27.1, 24.9, 22.6, 14.1; ESI-MS: calcd. for $C_{28}H_{44}O_5Cl_2S$: $[M+Na]^+$ 585.2184. Found: 585.2188.

Second-eluting trans: $R_f$=0.26; IR (ZnSe, cm$^{-1}$) 3040, 2927, 2855, 1734, 1456, 1179, 697 cm$^{-1}$; $^1$H NMR: δ 7.37-7.32 (m, 5H), 5.11 (s, 2H), 4.84 (dd, J=8.4, 0.8 Hz, 1H), 3.19 (s, 3H), 2.76-2.65 (m, 2H), 2.35 (t, J=7.6 Hz, 2H), 1.67-1.32 (26H), 0.89 (t, J=6.8 Hz, 3H); $^{13}$C NMR δ 173.6, 136.1, 128.5 (two overlapping signal), 128.2 (two overlapping signal), 86.4, 85.7, 66.1, 50.5, 41.1, 39.5, 34.3, 31.8, 29.6, 29.31, 29.25, 29.2, 29.0, 28.3, 28.1, 27.6, 27.0, 24.9, 22.7, 14.1: ESI-MS; calcd. for $C_{28}H_{44}O_5Cl_2S$: $[M+Na]^+$ 585.2184. Found: 585.2205.

First-eluting cis: $R_f$=0.26; IR (ZnSe, cm$^{-1}$) 2926, 2855, 1736, 1456, 1182, 697 cm$^{-1}$; $^1$H NMR: δ 7.37-7.32 (m, 5H), 5.33 (app d, J=9.6 Hz, 1H), 5.11 (s, 2H), 3.19 (s, 3H), 2.80-2.72 (bm, 2H), 2.36 (app t, J=7.6 Hz, 2H), 1.70-1.63 (m, 4H), 0.87 (t, J=6.8 Hz, 3H); $^{13}$C NMR δ 173.6, 136.0, 128.5 (two overlapping signal), 128.1 (two overlapping signal), 88.9, 80.7, 66.0, 49.5, 40.2, 39.2, 34.2, 31.8, 29.7, 29.3, 29.3, 29.2, 29.0, 28.8, 26.7, 25.7, 24.8, 23.7, 22.6, 14.1: HRFAB-MS (3-NBA matrix): calcd. for $C_{28}H_{45}O_5Cl_2S$: $[M+H]^+$563.2365. Found: 563.2349.

Second-eluting cis: $R_f$=0.21; IR (ZnSe, cm$^{-1}$) 2925, 2855, 1735, 1457, 1181, 697 cm$^{-1}$; $^1$H NMR: δ 7.36-7.32 (m, 5H), 5.33 (app d, J=9.6 Hz, 1H), 5.11 (s, 2H), 3.20 (s, 3H), 2.80-2.69 (bm, 2H), 2.34 (app t, J=7.6 Hz, 2H), 1.74-1.60 (4H), 1.50-1.19 (22H); $^{13}$C NMR δ 173.6, 136.1, 128.5 (two overlapping signal), 128.1 (two overlapping signal), 89.0, 80.7, 66.0, 49.5, 40.2, 39.3, 34.2, 31.8, 29.5, 29.5, 29.3, 29.2, 28.9, 28.9, 28.7, 26.8, 25.7, 24.8, 23.7, 22.6, 14.1; HRFAB-MS (3-NBA matrix): calcd. for $C_{28}H_{45}O_5Cl_2S$: $[M+H]^+$ 563.2365. Found: 563.2360.

1-(Octanoic acid, 8-yl)-2-octylcyclobutene (1) was prepared from the unpurified dichloromethanesulfonate using a reported procedure (see Baldwin, J. D. and Belfield, K. D. *J Org. Chem.* 1987, 52, 4772-4776; and Powers, D. C. et al. *J. Org. Chem.* 2007, 72, 187-194). NH$_3$ (~15 mL, liquid) was condensed into a 100-mL three-necked round bottom flask fitted with a dry ice/acetone condenser. Sodium (0.1127 g, 4.90 mmol, sliced under Hex) was added in small pieces. The resulting deep blue solution was stirred for 20 min. A solution of 0.2761 g (0.49 mmol) of the mixture of regioisomeric methanesulfonates S3 in anhydrous THF (1.5 mL) was added over 10 min. The reaction was removed from the dry ice bath and allowed to stir at −35° C. (refluxing NH$_3$) 5-30 min (depending on the scale of preparation). The reaction was then recooled to −78° C. (dry ice/acetone) and stirred for 2 h or until the starting material was consumed by TLC. Saturated aq. NH$_4$Cl was slowly added until the blue color was no longer visible. The condenser was removed and the reaction mixture was slowly allowed to warm to 0° C. with evaporation of NH$_3$. The remaining reaction mixture was diluted with 30 mL of water and the suspension was extracted with CH$_2$Cl$_2$ (3×50 mL). The organic layers were combined and washed sequentially with 1N aq. HCl/water/saturated aq. NaHCO$_3$/water/brine. The organic solution was then dried with NaSO$_4$, and concentrated under reduced pressure. The residue was purified by flash column chromatography using 10% EtOAc/Hex to afford the cyclobutene carboxylic acid (0.1312 g, 87%) as a low-melting white solid: $R_f$=0.50 (80:20:1 of Hex:EtOAc:AcOH); mp=33-35° C.; IR (ZnSe, cm$^{-1}$) 3493, 3036, 2923, 2853, 1708, 1467, 1275, 728 cm$^{-1}$; $^1$H NMR: δ 10.94 (br s, 1H, COOH), 6.17-6.15 (br m, 2H), 2.83-2.75 (br s, 2H), 2.35 (t, J=7.6 Hz, 2H), 1.68-1.60 (br m, 2H), 1.52-1.40 (br m, 2H), 1.35-1.20 (23H), 0.88 (t, J=6.8 Hz, 3H); $^{13}$C NMR (found 18 carbons) δ 180.6, 140.0, 139.9, 46.8, 46.7, 34.1, 31.9, 29.9, 29.8, 29.8, 29.7, 29.6, 29.5, 29.3, 29.3, 29.2, 29.0, 28.3, 28.2, 24.6, 22.7, 14.1; HRFAB-MS (Gly matrix): calcd. for $C_{20}H_{35}O_2$ 307.2637. Found [M−H]$^−$: 307.2636. Purity >99% by HPLC (retention time, 4.63 min).

cis-9,10-Ethanooctadecanoic acid (2). A solution of cyclobutene 1 (0.031 g, 0.1 mmol) and 10% Pd/C (0.02 g, 0.02 mmol) in EtOAc (1 mL) was placed in a vial under an atmosphere of H$_2$ and stirred at rt overnight (16 h). The mixture was then filtered through a plug of Celite and the plug was washed with approximately 10 mL of EtOAc. The solution was then evaporated under vacuum to afford 0.0297 g of the unprotected acid 2 (96%) as a colorless oil which was pure enough to use without chromatography: $R_f$=0.50 (80:20:1 of Hex:EtOAc:AcOH); IR (ZnSe, cm$^{-1}$): 3051 (br), 2921, 2852, 1708 cm$^{-1}$; $^1$H NMR: δ10.93 (br s, 1H, COOH), 2.35 (t, J=7.3, 2H), 2.24 (br s, 2H), 2.00-1.90 (br m, 1H), 1.64 (quintet J=7.3, 2H), 1.60-1.50 (m, 2H), 1.45-1.10 (br m, 24H), 0.88 (br t, J=7.0 Hz, 3H); $^{13}$C NMR: δ 180.2, 37.7, 37.6, 34.1, 31.9, 30.11, 30.05, 29.9, 29.7, 29.7, 29.4, 29.3, 29.1, 27.64, 27.55, 24.8, 24.7, 22.7, 14.1; HRCI-MS: calcd. for $C_{20}H_{38}O_2$: $[M+H]^+$311.2950. Found: 311.2949. Purity 100% by HPLC (retention time, 4.56 min).

2-(Octanoic acid benzyl ester, 8-yl) 3-octylcyclobutanone and 3-(Octanoic acid benzyl ester, 8-yl) 2-octylcyclobutanone (OA5) was prepared by a modification of a known procedure (see Powers, D. C. et al. *J Org. Chem.* 2007, 72, 187-194). To a solution of the regioisomeric dichloroketones OA2 (0.67 g, 1.4 mmol) in glacial acetic acid (3 mL) was added Zn(Cu) (0.45 g, 6.9 mmol). The mixture was stirred at rt under N$_2$ until TLC showed complete disappearance of stating material (~5 h). The reaction mixture was then filtered through a plug of Celite and washed with ether. The filtrate was washed sequentially with saturated aq. NaHCO$_3$ and water, and dried over Na$_2$SO$_4$. The residue obtained upon concentration was purified by flash chromatography on silica gel (5% EtOAc in Hex) to afford 0.388 g (87%) of a mixture of regioisomeric cyclobutanones OA5 as a colorless oil: $R_f$=0.41 (10% EtOAc/Hex); IR (ZnSe, cm$^{-1}$) 3034, 2923, 2853, 1774, 1735, 1161, 696 cm$^{-1}$; $^1$H NMR: δ 7.36-7.26 (br m, 5H), 5.115 (s, 2H), 3.28-3.17 (br m, 1H), 3.15-3.05 (br m, 1H), 2.51-2.43 (m, 1H), 2.42-2.32 (br m, 1H), 2.35/2.34 (overlapping t, J=7.53 Hz, 2H), 1.70-1.50 (br m, 4H), 1.45-1.14 (br m, 22H), 0.88/0.87 (overlapping t, J=7.19 Hz, 3H); $^{13}$C NMR δ 212.0, 173.6, 136.1, 128.5, 128.1, 66.0 (br s), 61.9/61.8 (two app s), 50.1/50.1 (two app s), 34.2, 31.8, 30.1, 30.0, 29.6, 29.6, 29.5, 29.4, 29.4, 29.23, 29.17, 29.0, 28.2, 28.08, 28.05, 27.98, 27.6, 24.9, 24.3, 24.3, 22.6, 14.1; HREI-MS: calcd. for $C_{27}H_{41}O_3Na$, 437.3032. Found $[M+Na]^+$: 437.3029.

2-(Octanoic acid, 8-yl) 3-octylcyclobutanone and 3-(octanoic acid, 8-yl) 2-octylcyclobutanone (3). A solution of the cyclobutanone OA5 (0.0391 g, 0.09 mmol) and 10% Pd/C (0.020 g, 0.18 mmol) in anhydrous MeOH (1 mL) in a vial was placed under an atmosphere of H$_2$ and stirred at rt overnight (16 h). The mixture was then concentrated under vacuum. The residue was resuspended in EtOAc (~20 mL) and filtered through a plug of Celite. The residue obtained upon concentration was purified by flash column chromatography on silica gel (10%/25% EtOAc/Hex) to afford 0.0267 g of the carboxylic acid 3 (87%) as a colorless oil: $R_f$=0.16 (25% EtOAc/Hex); IR (ZnSe, cm$^{-1}$) 3322 (br), 2926, 2856, 1776, 1709, 913, 749 cm$^{-1}$; $^1$H NMR: δ 3.28-3.18 (br m, 1H), 3.13/3.09 (overlapping dd, J=9.6, 3.1 and 9.0, 3.5, 0.56H/0.44H), 2.50/2.46 (two app abnormal-shape quintets, 0.55H/0.52H), 2.42 (br dd, J=9.6, 4.5 Hz, 1H), 2.35/2.34 (two app t, J=7.45 Hz, 2H), 1.63-1.54 (br m, 4H), 1.43-1.18 (br in, 22H), 0.88/0.87 (overlapping br t, J=7.0 Hz, 3H); $^{13}$C NMR: δ 212.1, 179.9, 62.0/61.9 (two app s), 50.20/50.17 (two app s), 34.0, 31.9, 30.1, 30.1, 29.7, 29.6, 29.6, 29.4, 29.3, 29.2, 29.02, 28.98, 28.2, 28.1, 28.0, 27.6, 24.6, 24.3, 24.3, 22.7, 14.1; HREI-MS: calcd. for $C_{20}H_{36}O_3Na$, 347.2557. Found [M+Na]$^+$: 347.2557. Purity >97% by HPLC (retention time, 6.82 min).

2-(Octanoic acid benzyl ester, 8-yl) 3-octylcyclobutanol and 3-(Octanoic acid benzyl ester, 8-yl) 2-octylcyclobutanol (OA6). To a –10° C. (ice/NaCl bath) solution of the cyclobutanone OA5 (0.037 g, 0.07 mmol) in anhydrous MeOH (1.5 mL) was added NaBH$_4$ (0.005 g, 0.15 mmol) under N$_2$. The reaction mixture was stirred at –10° C. until no starting material remained on TLC (20 min). The reaction was diluted with about 5 mL CH$_2$Cl$_2$ and quenched with 2 mL sat. NaHCO$_3$. The mixture was stirred for 10 min. The organic layer was removed and the aqueous layer was extracted with CH$_2$Cl$_2$ (3×5 mL). The organic layers were combined, dried over with Na$_2$SO$_4$, and evaporated to afford the alcohol as a colorless oil (0.029 g, 99%). Although the crude product appears pure by $^1$H NMR, it is actually a mixture of two regioisomers, each a 70:30 mixture of the 1,2,3-cis/cis and the 1,2-trans-2,3-cis isomers (isomer identities established through 2D-NMR). The individual isomers can be detected by TLC in 20% EtOAc/Hex: R$_f$=0.50 (major, all cis), 0.45 (major, all cis), 0.39 (minor, OH is trans to backbone), and 0.37 (minor, OH is trans to backbone); IR (ZnSe, cm$^{-1}$) 3396 (br), 2922, 2852, 1737, 1156, 732, 696 cm$^{-1}$; $^1$H NMR: δ 7.39-7.28 (br m, 5H), 5.14 (s, 2H), 4.23 br q, J=7.3, 0.714), 3.93 (br q, J=7.3, 0.3H), 2.42-2.36 (overlapping signal, 1H), 2.37 (t, J=7.6, 2H), 2.15-1.95 (br m, 1H), 1.90-1.78 (br m, 1H,), 1.70-1.60 (br m, 2H), 1.60-1.48 br m, 2H), 1.45-1.20 (br m, 22H), 0.90 (br t, J=7.6, 2H); $^{13}$C NMR: δ 173.68/173.65 (overlapping), 136.1, 128.5, 128.1, 72.2, 66.09/66.06 (two overlapping s), 66.0, 43.97/43.95 (overlapping), 37.3, 34.3, 31.9, 30.7, 30.6, 30.2, 29.94, 29.87, 29.8, 29.7, 29.62, 29.58, 29.5, 29.33, 29.29, 29.2, 29.14, 29.08, 29.0, 27.7, 27.6, 24.90, 24.88, 23.4, 23.3, 22.7, 14.1; HRESI-MS: calcd. for $C_{27}H_{44}O_3Na$, 439.3188. Found [M+Na]$^+$: 439.3174.

2-(Octanoic acid, 8-yl) 3-octylcyclobutanol and 3-(Octanoic acid, 8-yl) 2-octylcyclobutanol (4) were prepared as a mixture (0.0158 g, 81%) from benzyl ester(s) OA6 (0.0247 g, 0.06 mmol), 10% Pd/C (0.0126 g, 0.012 mmol) and EtOAc (0.6 mL) using a similar procedure as described for compound 2. Although the product, which is a colorless oil, is assumed to be a similar mixture of regio- and stereoisomers as was present in the benzyl ester precursor, the individual isomers are not separable: R$_f$=0.32 (4:6:0.05 of EtOAc:Hex:AcOH); IR (ZnSe, cm$^{-1}$) 3309 (br), 2922, 2853, 1709 cm$^{-1}$; $^1$H NMR: δ 4.22 (q, J=7.6, 0.7H, assumed —OH is cis to backbone from the characterization of starting material), 3.92 (q, J=7.6, 0.3H, assumed OH is trans to backbone), 2.43-2.33 (br m, 1H), 2.34 (t, J=7.3, 2H), 2.18-1.92 (m), 1.84 (br septet, J=8.0, 1H), 1.68-1.58 (br quintet, J=7.0, 2H), 1.58-1.48 (br m, 2H), 1.43-1.18 (br m, 22H), 0.88 (br t, J=7.0 Hz, 3H); $^{13}$C NMR: δ 179.50/179.46 (two app s), 72.28, 66.16/66.12 (two app s), 48.87/48.79 (two app s), 43.97, 37.26, 35.06, 33.98, 31.89, 30.69/30.62, 30.24, 30.18, 29.90, 29.87, 29.79, 29.74, 29.63, 29.60, 29.51, 29.46, 29.34, 29.31, 29.21, 29.11, 29.06, 29.01, 28.99, 28.97, 28.67, 28.60, 28.05, 27.95, 27.92, 27.73, 27.60, 24.66/24.63, 23.38/23.34, 22.67, 14.10; HRESI-MS: calcd. for $C_{20}H_{38}O_3Na$, 349.2719. Found [M+Na]$^+$: 349.2715. Purity >99% by HPLC (retention time, 11.8 and 15.9 min).

2-Chloro-4-(octanoic acid benzyl ester, 8-yl)-3-octylcyclobutanone; 2-Chloro-3-(octanoic acid benzyl ester, 8-yl) 4-octylcyclobutanone (OA7) was prepared based on a modification of a known procedure. To a solution of dichloroketone OA2 (0.9917 g, 2.1 mmol) in 4 mL of glacial acetic acid was added Zn dust (0.1475 g, 23 mmol). [Note: The amount of Zn required depended upon the purity of the dichlorocyclobutanone. In most cases, it was necessary to add a second equivalent after approximately 12 h of reaction.] The mixture was stirred at rt under N$_2$ until complete disappearance of the starting material was observed (16 h, TLC). The reaction mixture was then cooled in an ice bath and diluted with water (20 mL). The resulting solution was extracted with EtOAc (3×50 mL) and the combined organic layers were washed sequentially with water (2×100 mL) and saturated NaHCO$_3$ solution (2×50 mL). The resulting organic layer was dried over Na$_2$SO$_4$ and concentrated under reduced pressure to furnish a colorless oil (0.8948 g, 97% crude yield) as a 1:1 mixture of regioisomers, each a 9:1 mixture of cis/trans stereoisomers ($^1$H NMR); the mixture was used directly in the next step. Analysis of the $^1$H NMR indicated that the expected product was accompanied by recovered starting material OA2 (approximately 14%) and the cyclobutanone OA5 (overreduction product, approximately 10%). These byproducts could not be removed by flash chromatography. R$_f$=0.58/0.53 (major), 0.48/0.43 (minor) (10% EtOAc in Hex); IR (ZnSe, cm$^{-1}$) 3036, 2925, 2854, 1789, 1735, 1456, 1162, 696 cm$^{-1}$; $^1$H NMR: δ 7.36-7.25 (m, 5H), 5.12/5.11 (overlapping s, 2H), 4.97 (dd, J=2.6, 9.5, 0.1H), 4.51 (dd, J=2.8, 7.6 Hz, 0.9H), 3.35-3.20 (m, 1.1H), 2.75-2.65 (m, 0.1H), 2.53-2.40 (m, 0.9H), 2.36/2.35 (overlapping t, J=7.2 Hz, 2H), 1.75-1.20 (m, 26H), 0.92-0.85 (m, 3H); $^{13}$C NMR δ 203.48/203.45, 173.5, 136.1, 128.5, 128.1, 66.0, 65.7, 58.3, 58.2, 40.74/40.72, 34.18, 31.77/31.75, 29.5, 29.3, 29.24, 29.16, 29.14, 29.13, 29.02, 28.97, 28.90, 28.86, 28.02, 27.96, 27.92, 27.87, 25.64/25.57, 24.80/24.78, 22.59/22.58, 14.0; HRESI-MS: calcd. for $C_{27}H_{41}O_3ClNa$, 471.2642. Found [M+Na]$^+$: 471.2635.

2-Chloro-4-(octanoic acid, 8-yl) 3-octylcyclobutanone-; 2-Chloro-3-(octanoic acid, 8-yl) 4-octylcyclobutanone (5) was prepared in a similar manner as compound 2. The benzyl ester OA7 (0.085 g, 0.19 mmol), 10% Pd/C (0.040 g, 0.038 mmol) and EtOAc (1.9 mL) were used to afford 0.0478 g of the unprotected acid 5 (70%) as a colorless oil after purification by flash column chromatography (20% EtOAc/Hex). The product also contain approximately 5% of an inseparable trans-chlorocyclobutanone 7 byproduct ($^1$H NMR signal at δ 4.37) probably arising from the epimerization of cis-chlorocyclobutanone 5: R$_f$=0.19 (4:1 Hex:EtOAc); IR (ZnSe, cm$^{-1}$) 3036, 2924, 2854, 1788, 1706, 1461 cm$^{-1}$; $^1$H NMR: δ 10.74 (br s, 1H, COOH), 4.96 (dd, J=9.4, 2.6, 0.05H), 4.50 (dd, J=7.6, 2.8, 0.95H), 3.35-3.20 (m, 1.05H), 2.46 (quintet, J=8.1, 0.95H), 2.74-2.62 (m, 0.05H), 2.35/2.33 (overlapping t, J=7.3, 2H), 1.80-1.15 (m, 22H), 0.88/0.87 (overlapping t, J=6.9, 3H); $^{13}$C NMR δ 203.62/203.56, 180.1, 65.7, 58.30/58.26, 401.8, 34.0, 31.8, 29.5, 29.4, 29.3, 29.18/29.15, 29.04/29.00, 28.9, 28.04/27.98, 27.95/27.90, 25.67/25.59, 24.5, 22.6, 14.1; HRESI-MS: calcd. for $C_{20}H_{35}O_3ClNa$, 381.2172. Found [M+Na]$^+$: 381.2191.

(E)-9-octadecenoic acid, benzyl ester (benzyl elaidate) was prepared from the reaction of elaidic acid (0.9836, 3.5 mmol), DCC (0.79 g, 3.8 mmol), DMAP (0.087 g, 0.7 mmol), and benzyl alcohol (0.73 mL, 7 mmol) in CH$_2$Cl$_2$ (10 mL) by a similar procedure as employed for benzyl oleate. The product was purified by flash column chromatography on silica gel (2.5%/5% EtOAc/Hex) to afford 1.2280 g (95%) of benzyl elaidate as a colorless oil: Rf=0.57 (10% EtOAc/Hex). IR (ZnSe, cm$^{-1}$) 2922, 2852, 2737, 1160, 966, 696 cm$^{-1}$; $^1$H NMR: δ 7.38-7.34 (m, 5H), 5.41-5.38 (m, 2H), 5.13 (s, 2H), 2.37 (t, J=7.2 Hz, 2H), 1.98 (br s, 4H), 1.68-1.63 (m, 2H), 1.38-1.18 (br m, 20H), 0.90 (t, J=7.2 Hz, 3H); $^{13}$C NMR δ 173.6, 136.1, 130.4, 130.2, 128.5, 128.1, 66.0, 34.3, 32.57, 32.52, 31.9, 29.6, 29.52, 29.46, 29.3, 29.2, 29.1, 29.0, 28.9, 24.9, 22.7, 14.1.

2,2-Dichloro-4-(octanoic acid benzyl ester, 8-yl) 3-octyl-cyclobutanone-; 2,2-Dichloro-3-(octanoic acid benzyl ester, 8-yl) 4-octylcyclobutanone (EA2) was prepared based on a known procedure. To a mixture of Zn(Cu) (1.8443, 28 mmol) and benzyl elaidate EA1 (2.073 g, 5.6 mmol) in 11 mL of anhydrous ether was added over 2 h (syringe pump) trichloroacetyl chloride (2.0 mL, 18 mmol). The reaction mixture was stirred at rt for 5 h (or until the starting material is consumed by TLC) and filtered through a plug of Celite. The residue was washed with ether (20 mL). The combined ether layers were transferred to a round bottom flask and cooled over ice. The black solution was then diluted with 40 mL of water and 40 mL of sat. NaHCO$_3$. The mixture was allowed to warm to rt and stirred overnight. The aqueous layer was extracted with ether (3×50 mL) and the combined organic layers were dried over Na$_2$SO$_4$ and evaporated to dryness. The residue obtained upon concentration could be used for the next step without further purification or, alternatively, could be purified by rapid flash column chromatography through a short plug of silica (2.5%/5% EtOAc/Hex) to afford 1.6856 g (63%) of a yellow oil consisting of a 1:1 mixture of regioisomers: R$_f$=0.63 (20% EtOAc/Hex); IR (ZnSe, cm$^{-1}$) 2926, 2855, 1802, 1735, 1456, 1162, 696 cm$^{-1}$; $^1$H NMR: δ 7.47-7.23 (m, 5H), 5.120/5.117 (overlapping s, 2H), 3.158/3.126 (overlapping dt, J=7.2, 1.5 Hz, 1H), 2.56-2.46 (m, 1H), 2.37/2.34 (overlapping t, J=7.6 Hz, 2H), 1.96-1.18 (m, 26H), 0.90/0.87 (overlapping t, J=7.2 Hz, 3H); $^{13}$C NMR, 75 MHz: δ 196.3, 173.5, 136.0, 128.4, 128.1, 87.1, 66.0, 60.7, 60.6, 52.3, 34.2, 34.1, 31.8, 31.7, 31.37, 31.36, 29.42, 29.40, 29.3, 29.23, 29.20, 29.14, 29.12, 29.08, 28.93, 28.90, 28.85, 27.5, 27.4, 27.12, 27.05, 24.80, 24.78, 22.59, 22.57, 14.04, 14.03; HRESI-MS: calcd. for C$_{27}$H$_{40}$O$_3$Cl$_2$Na [M+Na]$^+$: 505.2252 Found: 505.2248.

2,2-Dichloro-4-(octanoic acid benzyl ester, 8-yl) 3-octyl-cyclobutanol; 2,2-Dichloro-3-(octanoic acid benzyl ester, 8-yl) 4-octylcyclobutanol (EA3) was prepared by a similar procedure as OA3. Dichlorocyclobutanone EA2 (0.2100 g, 0.4 mmol), NaBH$_4$ (0.055 g, 1.5 mmol), and iPrOH 6 mL was obtained the product purified by flash column chromatography with 5% EtOAc/Hex to afford the mixture of 1:1 regioisomer EA3 0.1659 g (85%) as a colorless oil: R$_f$=0.66 (minor)/0.61 (major)/0.56 (minor)/0.51 (major) (10% EtOAc/Hex). IR (ZnSe, cm$^{-1}$): 3459 (br), 2924, 2853, 1736, 1456, 1161, 734, 696 cm$^{-1}$; $^1$H NMR: δ 7.36-7.31 (m, 5H), 5.12 (s, 2H), 4.37 (br d, J=6.4 Hz, 0.4H), 3.91 (br d, J=8.0 Hz, 0.6H), 2.80-2.45 (br m, 211), 2.37/2.36 (overlapping t, J=7.6 Hz, 2H), 1.80-1.05 (br m, 26H), 0.89/0.88 (overlapping t, J=6.7 Hz, 3H). Small quantities of individual isomers could be separated for analysis by flash column chromatography using 10% EtOAc/Hex. The stereochemical assignments were assigned by 2D-NMR experiments including COSY, NOESY, and HSQC.

first-eluting H$_1$-H$_3$ trans: R$_f$=0.66; IR (ZnSe, cm$^{-1}$): 3463 (br), 2927, 2855, 1738, 1453, 1158 cm$^{-1}$; $^1$H NMR: δ 7.37-7.31 (m, 5H), 5.12 (s, 2H), 4.38 (ddd, $^3J_{H1,H4}$=6.8 Hz, $^3J_{H1,OH}$=5.1 Hz, $^4J_{H1,H3(trans)}$=1.3 Hz, 1H, CH—OH), 2.62-2.55 (m, 1H, CH—CCl$_2$), 2.44 (d, $^3J_{H1,OH}$=5.1 Hz, —OH), 2.36 (t, J=7.6 Hz, 2H), 2.18-2.08 (m, 1H, CH—CHOH), 1.80-1.10 (br m, 26H), 0.89 (t, J=6.7 Hz, 3H); $^{13}$C NMR: δ 173.6, 136.1, 128.5, 128.2, 90.2, 78.5, 66.1, 57.0, 42.0, 34.3, 31.9, 31.3, 29.7, 29.5, 29.4, 29.3, 29.0, 27.7, 27.5, 26.6, 24.9, 22.7, 14.1; HRESIMS: calcd. for C$_{27}$H$_{40}$O$_3$Cl$_2$: [M+Na]$^+$ 507.2409. Found: 507.2409.

first-eluting H$_1$-H$_3$ cis: R$_f$=0.61; IR (ZnSe, cm$^{-1}$): 3448 (br), 2925, 2854, 1737, 1456, 1163, 734, 697 cm$^{-1}$; $^1$H NMR: δ 7.37-7.31 (m, 5H), 5.12 (s, 2H), 3.91 (dd, $^3J_{H1,OH}$=10.8 Hz, $^3J_{H1,H4(trans)}$=8.0 Hz, $^4J_{H1,H3(cis)}$=0 Hz, 1H, CH—OH), 2.46 (d, J=10.8 Hz, 2H, OH), 2.36 (t, J=7.6 Hz, 2H), 2.11-2.04 (m, 1H, CH—CCl$_2$), 1.75-1.18 (m, 27H), 0.88 (t, J=6.8 Hz, 3H); $^{13}$C NMR, 75 MHz: δ 173.6, 136.1, 128.5, 128.2, 91.0, 81.6, 66.1, 51.9, 48.1, 34.3, 33.0, 31.8, 30.0, 29.6, 29.41, 29.38, 29.2, 29.0, 27.3, 26.8, 24.9, 22.6, 14.1; HRESIMS: calcd. for C$_{27}$H$_{40}$O$_3$Cl$_2$: [M+Na]$^+$ 507.2409. Found: 507.2415.

Second-eluting H$_1$-H$_3$ trans: R$_f$=0.56; IR (ZnSe, cm$^{-1}$): 3463 (br), 2925, 2854, 1736, 1456, 1163, 696 cm$^{-1}$; $^1$H NMR: δ 7.36-7.31 (m, 5H), 5.11 (s, 2H), 4.40-4.34 (m, 1H), 2.64-2.55 (m, 1H, CH—OH), 2.64-2.55 (m, 1H, CH—CCl$_2$), 2.46 (d, J=4.8 Hz, 1H, OH), 2.35 (t, J=7.6 Hz, 2H), 2.20-2.03 (m, 1H, CH—CHOH), 1.80-1.10 (br m, 26H), 0.88 (t, J=6.4 Hz, 3H); $^{13}$C NMR, 75 MHz: δ 173.7, 136.1, 128.5, 128.2, 90.2, 78.4, 66.1, 57.0, 42.0, 34.3, 31.9, 31.3, 29.6, 29.5, 29.41, 29.39, 29.2, 29.1, 29.0, 27.6, 27.5, 26.7, 24.9, 22.7, 14.1; HRESIMS: calcd. for C$_{27}$H$_{40}$O$_3$Cl$_2$: [M+Na]$^+$507.2409. Found: 507.2398.

Second-eluting H$_1$-H$_3$ cis: R$_f$=0.51; IR (ZnSe, cm$^{-1}$): 3444 (br), 2924, 2854, 1734, 1162, 734, 696 cm$^{-1}$; $^1$H NMR: (57.37-7.31 (m, 5H), 5.11 (s, 2H), 3.90 (dd, $^3J_{H1,OH}$=10.8 Hz, $^3J_{H1,H4(trans)}$=8.0 Hz, $^4J_{H1,H3(cis)}$=0 Hz, 1H, CH—OH), 2.52 (OH, d, J=10.8 Hz, 2H), 2.35 (t, J=7.6 Hz, 2H), 2.13-2.02 (in, 1H, CH—CCl$_2$), 1.75-1.18 (m, 27H), 0.89 (t, J=6.8 Hz, 3H); $^{13}$C NMR, 75 MHz: δ 173.7, 136.1, 128.5, 128.1, 91.0, 81.6, 66.1, 51.9, 48.0, 34.2, 33.0, 31.8, 30.0, 29.6, 29.4, 29.3, 29.2, 29.02, 28.97, 28.9, 27.2, 26.8, 24.9, 24.8, 22.6, 14.1; HRESIMS: calcd. for C$_{27}$H$_{40}$O$_3$Cl$_2$: [M+Na]$^+$507.2409. Found: 507.2409.

2,2-Dichloro-4-(octanoic acid benzyl ester, 8-yl) 3-octyl-cyclobutanol, methanesulfonate ester; 2,2-Dichloro-3-(octanoic acid benzyl ester, 8-yl) 4-octylcyclobutanol, methanesulfonate ester (EA4) was prepared similarly to OA4 from reaction of methanesulfonyl chloride (0.05 mL, 0.7 mmol), cyclobutanol EA3 (0.1659 g, 0.3 mmol), and triethylamine (0.20 mL, 1.7 mmol) in CH$_2$Cl$_2$ (2 mL). The crude product was purified by flash chromatography (5% EtOAc/Hex) to provide dichloro mesylate EA4 as a light yellow oil (0.1456 g, 86%) which included several inseparable isomers: R$_f$=0.40/0.38 (20% EtOAc/Hex); IR (ZnSe, cm$^{-1}$): 2925, 2851, 1734, 1368, 1180, 964, 697 cm$^{-1}$; $^1$H NMR: δ 7.38-7.30 (m, 5H), 5.20 (dd, J=7.1, 1.2 Hz, 0.4H), 5.115/5.112 (two overlapping s, total 2H), 4.84 (d, J=8.8 Hz, 0.6H), 3.202/3.199 (two overlapping s, 1.8H), 3.166/3.163 (two overlapping s, total 1.2H), 2.66-2.58 (m, 0.4H), 2.40-2.30 (m, 2H), 2.21-2.12 (m, 0.6H), 2.10-1.98 (m 0.6H), 1.80-1.15 (m, 26.4H), 0.91-0.86 (m, 3H); $^{13}$C NMR δ 173.6, 136.10/136.08, 128.5/128.1, 86.45/86.38, 84.09, 83.86/83.82, 66.03/66.01, 57.18, 51.81/51.80, 44.51/44.50, 41.71, 39.5, 39.0, 34.2, 32.21/32.18, 31.78/31.77, 31.41/31.36, 30.1, 29.49 29.46, 29.42, 29.34, 29.32, 29.27, 29.22, 29.16, 28.95, 28.90, 28.2, 27.0, 26.9, 26.8, 26.7, 26.6, 26.5, 26.4, 26.3, 24.8, 22.6, 14.1; HRESI-MS: C$_{28}$H$_{44}$O$_5$Cl$_2$SNa: [M+Na]$^+$585.2184. Found: 585.2186.

1-(Octanoic acid, 8-yl)-2-octylcyclobutene (6) was prepared similarly to compound 1 from reductive fragmentation and deprotection of dichloromethansulfonate EA4 (0.1430, 0.25 mmol) in THF (1 mL), NH$_3$ (~10 mL), Na (~0.09 g, 4.1 mmol). The crude product was purified by flash chromatography (10% EtOAc/Hex) to afford the acid 6 (0.0352 g, 46%) as a colorless oil: $R_f$=0.35 (60:40 of Hex:EtOAc); IR (ZnSe, cm$^{-1}$) 3124, 2923, 2852, 1708, 910, 736 cm$^{-1}$; $^1$H NMR: δ 6.12 (br s, 2H), 2.35 (t, J=7.2 Hz, 2H), 2.26 (t, J=7.2 Hz, 2H), 1.64 (quintet, J=7.2 Hz, 2H), 1.44 (br m, 4H), 1.35-1.20 (23H), 0.88 (t, J=6.8 Hz, 3H); $^{13}$C NMR δ 179.7, 139.2, 139.1, 50.4, 50.3, 34.02, 33.97, 31.9, 29.9, 29.6, 29.3, 29.2, 29.0, 28.4, 28.3, 24.7, 22.7, 14.1; HRFAB-MS (3-NBA matrix): calcd. for $C_{20}H_{35}O_2Li_2$ 321.2957. Found [M−H+2Li]$^+$: 321.2969. Purity 100% by HPLC (retention time, 4.73 min).

2-Chloro-4-(octanoic acid benzyl ester, 8-yl) 3-octylcyclobutanone-; 2-Chloro-3-(octanoic acid benzyl ester, 8-yl) 4-octylcyclobutanone EA5 was prepared similarly to the procedure described for compound OA7. Reaction of benzyl ester EA2 (0.50 g, 1.0 mmol), Zn(Cu) (0.0744 g, 1.1 mmol) and glacial acetic acid (2 mL) furnished, after flash chromatography (5% EtOAc/Hex), trans-monochlorocyclobutanone EA5 (0.3126 g, 70%) as a colorless oil which included an equal mix of the 2-chloro-4-octyl and 2-chloro-3-octyl regioisomers, each of which included both epimers at the chloride-bearing carbon: $R_f$=0.42/0.39 (minor) and 0.33 (major) (10% EtOAc/Hex).

The amount of Zn dust varied from 1.1-2.2 equiv; generally, a second equivalent of zinc dust was added to the incomplete reaction mixture after stirring for approximately 12 h. The residual dichlorocyclobutanone was easily removed by flash column chromatography. However, the cyclobutanone product of overreduction was formed in significant amounts (28% based upon $^1$H NMR and was nearly inseparable by flash column chromatography: IR (ZnSe, cm$^{-1}$) 2924, 2854, 1788, 1735, 1457, 1161, 733, 696 cm$^{-1}$; $^1$H NMR: δ7.40-7.32 (m, 5H), 5.113/5.110 (overlapping s, 2H), 4.95 (dd, J=3.1, 9.4, 0.3H), 4.37 (dt, J=2.7, 7.8 Hz, 0.7H), 2.97-2.90 (m, 0.3H), 2.84-2.74 (m, 0.7H), 2.40-2.30 (overlapping m, 2.3H), 2.08-1.97 (m, 0.7H), 1.85-1.10 (m, 26H), 0.92-0.84 (m, 3H); $^{13}$C NMR δ 204.6, 202.0, 173.5, 136.1, 128.5, 128.1, 66.0, 65.52/65.46, 63.98, 63.78/63.75, 63.57/63.52, 60.74/60.69, 49.8, 43.7, 37.4, 36.63/36.59, 35.12/35.10, 34.2, 31.8, 31.3, 30.3, 30.1, 29.5, 29.42, 29.38, 29.32, 29.25, 29.19, 29.03, 29.00, 28.96, 28.93, 28.88, 28.2, 27.67, 27.60, 27.55, 27.48, 27.38, 27.3, 27.2, 27.1, 24.83/24.80, 22.6, 14.0; HRESI-MS: calcd. for $C_{27}H_{41}O_3ClNa$, 471.2642. Found [M+Na]$^+$: 471.2630.

2-Chloro-4-(octanoic acid, 8-yl) 3-octylcyclobutanone-; 2-Chloro-3-(octanoic acid, 8-yl) 4-octylcyclobutanone (7) was prepared similarly to compound 2. Reaction of benzyl ester EA5 (0.0337 g, 0.11 mmol), with 10% Pd/C (0.0236 g, 0.022 mmol) and EtOAc (1 mL) afforded 0.0127 g of the unprotected acid (54%) as a white solid: $R_f$=0.24 (6:4:0.05 of Hex:EtOAc:AcOH); mp.=74-75° C.; IR (ZnSe, cm$^{-1}$) 3062, 2924, 2854, 1789, 1708, 1464 cm$^{-1}$; $^1$H NMR: δ 8.70 (br s, 1H), 4.95 (dd, J=2.9, 9.2, 0.3H), 4.37 (ddd, J=7.8, 2.5, 1.3, 0.7H), 2.97-2.91 (m, 0.3H), 2.85-2.73 (m, 0.7H), 2.40-2.22 (m, 22H), 2.11-2.98 (m 0.7H), 1.85-1.10 (m 26H), 0.92-0.82 (m, 3H); $^{13}$C NMR δ 211.7, 204.7, 202.2, 179.9, 65.6/65.5, 64.0, 63.85/63.82, 63.64/63.58, 60.82/60.77, 49.81, 43.8, 37.5, 36.69/36.65, 35.2, 34.0, 31.8, 31.3, 30.4, 30.2, 29.55, 29.48, 29.44, 29.38, 29.31, 29.25, 29.2, 29.06, 29.06, 28.9, 28.3, 28.2, 27.73, 27.67, 27.62, 27.44, 27.37, 27.26, 27.20, 27.17, 24.63/24.60, 22.7, 14.1; HRESI-MS: calcd. for $C_{20}H_{35}O_3ClNa$, 381.2172. Found [M+Na]$^+$: 381.2170.

Benzyl 9-decenoate (DA1) was prepared by a known procedure.[1] Thionyl chloride (36.9 mL, 51 mmol) was added to a stirred solution of 9-decenoic acid DA (8.67 g, 51 mmol) and catalytic dimethylformamide (DMF, 0.12 mL, 1.5 mmol) in toluene (400 mL). The reaction was stirred at rt until the starting material was consumed (TLC, 24 h). The reaction was concentrated and the residue redissolved in toluene (400 mL) and triethylamine (8.5 mL). The solution was stirred for 24 h and washed with water. The aqueous layer was then extracted with ether. The combined organic solution were combined, dried with $Na_2SO_4$, and concentrated under vacuum. The residue was purified by flash column chromatography on silica gel (5-10% EtOAc in Hex) to give benzyl 9-decenoate DA1 (13.1 g, 99%) as a colorless oil: $R_f$=0.40 (10% EtOAc/Hex); IR (ZnSe, cm$^{-1}$): 3072, 2927, 2855, 1734, 1161, 908, 730 cm$^{-1}$; $^1$H NMR: δ 7.38-7.32 (m, 5H), 5.83 (ddt, J=17, 10.2, 6.6 Hz, 1H), 5.14 (s, 2H), 5.02 (ddd, J=7.6 Hz, 2H), 5.00 (dq, J=17.0, 1.7 Hz, 1H), 4.96 (d of quintet, J=10.2, 1.2 Hz, 1H), 2.37 (t, J=7.3 Hz, 2H), 2.10-2.02 (br q, J=7.3 Hz, 2H), 1.70-1.63 (br m, 2H), 1.41-1.48 (m, 10H); $^{13}$C NMR: δ 173.5, 138.9, 136.1, 128.4, 128.1, 128.0, 114.1, 65.9, 34.2, 33.7, 28.99, 28.97, 28.8, 28.7, 24.8, 22.6, 14.0; HRESI-MS: calcd. for $C_{17}H_{24}O_2Na$: [M+Na]$^+$283.1674. Found: 283.1671.

3-(Octanoic acid, 8-yl, benzyl ester) 2,2-dichlorocyclobutanone DA2 was prepared similarly to compound OA2 and afforded (13.78 g, 80%) as a brown oil from benzyl 9-decenoate DA1 (12.36 g, 48 mmol), trichloroacetyl chloride (10.7 mL, 95 mmol), and Zn(Cu) (15.55 g, 238 mmol) in ether 0.1 M (340 mL) (Consistent with a previous report, only one isomer was observed. The assignment was confirmed by presence of geminal hydrogens adjacent to the ketone alpha ketone position at δ 3.33 and 2.94 by $^1$H-NMR and by the observation of eleven rather than twelve carbons (symmetry) upon dechlorination to cyclobutanone 10): $R_f$=0.34 (10% EtOAc/Hex); IR (ZnSe, cm$^{-1}$): 2935, 2852, 1814, 1730, 905, 725 cm$^{-1}$; $^1$H NMR: δ 7.39-7.29 (m 5H), 5.12 (s, 2H), 3.33 (dd, J=9.4, 17.2, Hz, 1H), 2.94 (dd, J=9.0, 17.2 Hz, 1H), 2.88-2.81 (m, 1H), 2.37/2.36 (overlapping t, J=7.5 Hz, 2H), 1.94-1.84 (m, 1H), 1.70-1.72 (m, 3H), 1.46-1.28 (m, 8H); $^{13}$C NMR δ 192.8, 173.4, 136.0, 128.4, 128.0, 88.8, 65.9, 47.7, 45.8, 34.1, 31.2, 29.0, 28.9, 28.8, 27.2, 24.7; HREI-MS: calcd. for $C_{19}H_{25}O_3Cl_2$: [M+H]$^+$ 371.1181. Found: 371.1188.

3-(Octanoic acid, 8-yl, benzyl ester) 2,2-dichlorocyclobutanol DA3 was prepared similarly to compound OA3 from the previous dichloroketone DA2 (10.0 g, 26.9 mmol), $NaBH_4$ (1.528 g, 40.4 mmol), and iPrOH (350 mL). The crude product was purified by flash column chromatography with 10% EtOAc/Hex to furnish the dichlorobutanol DA3 (5.76 g, 57%) as a colorless oil: $R_f$=0.39 (20% EtOAc/Hex); IR (ZnSe, cm$^{-1}$): 3440 (br), 2927, 2854, 1733, 1164, 960, 697 cm$^{-1}$; $^1$H NMR: δ 7.40-7.30 (m 5H), 5.12 (s, 2H), 4.73-4.64 (m, 0.1H) 4.34-4.27 (m, 0.9H), 2.97 (d, J=8.2 Hz 0.1H, OH is trans to backbone), 2.87 (d, J=10.3 Hz, 0.9H, OH is cis to backbone), 2.48-2.34 (m, 1H), 2.36 (t, J=7.6 Hz, 2H), 1.78-1.60 (m, 3H), 1.53-1.28 (m, 11H); $^{13}$C NMR δ 173.7, 136.0, 128.5, 128.1, 92.9, 75.4, 66.1, 45.6, 34.5, 34.2, 29.8, 29.2, 29.0, 28.9, 26.5, 24.8; HRESIMS: calcd. for $C_{19}H_{23}O_3Cl_2$: [M+Na]$^+$ 395.1157. Found: 395.1151.

3-(Octanoic acid, 8-yl, benzyl ester) 2,2-dichlorocyclobutanol, methanesulfonate ester DA4 was prepared similarly to compound OA4 from reaction of methanesulfonyl chloride (20 mL, 29.4 mmol), cyclobutanol DA3 (5.50 g, 14.7 mmol), and triethylamine (9.2 mL, 66.3 mmol) in $CH_2Cl_2$ (70 mL). The crude product was purified by flash chromatography (10% EtOAc/Hex) to afford DA4 as a light yellow oil (6.1340 g, 92%): $R_f$=0.36 (20% EtOAc/Hex); IR (ZnSe, cm$^{-1}$): 2927, 2858, 1731, 1364, 1179, 952 cm$^{-1}$; $^1$H NMR: δ 7.36-7.31 (m 5H), 5.11 (s, 2H), 5.13-5.09 (m, 1H), 3.18 (s, 3H), 2.56-2.50 (m, 2H), 2.35 (t, J=7.6 Hz, 2H), 1.93-1.28 (m, 13H); $^{13}$C NMR δ 173.5, 136.0, 128.4, 128.1, 88.4, 78.3, 66.0, 45.8, 39.3, 34.1, 31.6, 29.8, 29.1, 28.87, 28.85, 26.2, 24.8; HRESI-MS: calcd. for $C_{20}H_{28}O_5Cl_2SNa$: $[M+Na]^+$ 473.0932. Found: 473.0930.

8-(2-Cyclobuten-1-yl)-octanoic acid (8) was prepared by a similar procedure as 1 from reaction of Na metal (2.8 g, 120 mmol) with a solution of 5.4 g (12 mmol) of the mixture of dichloro mesylate DA4 in THF (30 mL) and $NH_3$ (~250 mL). The crude product was purified by flash column chromatography (2% EtOAc/Hex) to afford 9,10-ethenooctadecanoic acid (1.6367 g, 52%) as a low-melting white solid: $R_f$=0.47 (6:4:0.05 of Hex:EtOAc:AcOH); m.p.=20-21° C.; IR (ZnSe, cm$^{-1}$) 3112 (br), 3043, 2920, 2853, 1705, 697 cm$^{-1}$; $^1$H NMR: δ 10.27 (br s, 1H, COOH), 6.11 (br d, J=2.4 Hz, 1H), 6.04 (br dd, J=0.8, 2.0 Hz, 1H), 2.77 (m, 1H), 2.66 (ddd, J=0.8, 4, 13.2 Hz, 1H), 2.35 (t, J=7.2 Hz, 2H), 2.04 (d, J=13.2 Hz, 1H), 1.64 (quintet, J=7.2 Hz, 2H), 1.51-1.38 (br m, 2H), 1.38-1.23 (br m, 8H); $^{13}$C NMR δ 180.0, 141.1, 135.1, 44.2, 36.9, 34.6, 34.0, 29.5, 29.2, 29.0, 27.9, 24.7; HRESI-MS: calcd. for $C_{12}H_{20}O_2Na$ $[M+Na]^+$: 219.1361. Found: 219.1355. Purity 100% by HPLC (retention time, 5.01 min).

8-Cyclobutyloctanoic acid (9) was prepared by a similar procedure as for 2 from the hydrogenation of cyclobutene 8 (0.0339, 0.17 mmol), over 10% Pd/C (0.0367 g, 0.03 mmol) in EtOAc (1.7 mL) to afford 0.0301 g of the unprotected acid 9 (89%) as a low-melting white solid: $R_f$=0.47 (6:4:0.05 of Hex:EtOAc:AcOH); m.p.=28-30° C.; IR (ZnSe, cm$^{-1}$): 3035 (br), 2916, 2849, 1695, 909, 733 cm$^{-1}$; $^1$H NMR: δ 11.34 (br s, 1H, COOH), 2.37 (t, J=7.2 Hz, 2H), 2.25 (septet, J=7.2 Hz, 1H), 2.10-1.98 (m, 2H), 1.90-1.75 (m, 2H), 1.70-1.52 (m, 2H), 1.40-1.12 (br m, 10H); $^{13}$C NMR: δ 180.3, 37.0, 36.2, 34.1, 29.4, 29.2, 29.0, 28.4, 27.1, 24.7, 18.5; HRCI-MS: calcd. for $C_{12}H_{22}O_2$: $[M+H]^+$199.1698. Found: 199.1695. Purity >99% by HPLC (retention time, 4.92 min).

3-(Octanoic acid benzyl ester, 8-yl)cyclobutanone (DA5) was prepared similarly to oleate series. Dichloroketone DA2 (1.05 g, 2.69 mmol), 6 mL of glacial acetic acid, and Zn(Cu) (1.76 g, 26.9 mmol) were used and the product was purified by flash chromatography (10% EtOAc/Hex) to afford colorless oil 0.4859 g (59%) as a mixture of isomers: $R_f$=0.55 (20% EtOAc/Hex). IR (ZnSe, cm$^{-1}$) 2923, 2854, 2780, 2732, 1163, 730, 697 cm$^{-1}$; $^1$H NMR: δ 7.35-7.28 (br m, 5H), 5.09 (s, 2H), 3.13-3.03 (m, 2H), 2.65-2.57 (m, 2H), 2.33 (t, J=7.2, 2H), 2.33-2.26 (m, 1H), 1.68-1.58 (br quintet, J=6.4, 2H), 1.58-1.48 (br q, J=7.2, 2H), 1.29 (br s, 8H); $^{13}$C NMR: δ 208.2, 173.3, 134.0, 128.3, 127.9, 65.8, 52.3, 36.1, 34.0, 28.9, 28.8, 28.0, 24.7, 23.6; HRESI-MS: calcd. for $C_{19}H_{26}O_3Na$ $[M+Na]^+$: 325.1780. Found: 325.1775.

3-(Octanoic acid, 8-yl)cyclobutanone (10) was prepared similarly to compound 2: The benzyl ester DA5 (0.0346, 0.1 mmol), 10% Pd/C (0.020 g, 0.02 mmol) and EtOAc 1 mL were used and the product was purified by flash column chromatography on silica gel (step gradient of 20% to 40% EtOAc/Hex) to afford 0.0189 g of the unprotected acid 10 (90%) as low-melting white solid: $R_f$=0.3 (6:4:0.05 of Hex:EtOAc:AcOH); m.p.=35-37° C.; IR (ZnSe, cm$^{-1}$) 3094 (br), 2923, 2853, 1780, 1705 cm$^{-1}$; $^1$H NMR: δ 10.61 (br s, 1H, COOH), 3.17-3.08 (m, 2H), 2.69-2.61 (m, 2H), 2.35 (br t, J=7.6, 2H), 2.39-2.31 (br, 1H), 1.69-1.53 (br m, 4H), 1.32 (br s, 8H); $^{13}$C NMR: δ 208.8, 179.9, 52.5, 36.3, 34.0, 29.2, 29.1, 28.9, 28.2, 24.6, 23.8; HRCI-MS: calcd. for $C_{12}H_{20}O_3Na$, 213.1491. Found $[M+Na]^+$: 213.1490. Purity >97% by HPLC (retention time, 10.75 min).

3-(Octanoic acid benzyl ester)cyclobutanol (DA6) was prepared similarly to reduction of compound OA6: the mixed cyclobutanone DA5 (0.0509 g, 0.17 mmol) in anhydrous MeOH (2.5 mL) and $NaBH_4$ (0.0127 g, 0.34 mmol) were used to afford 0.0395 g (76%) of S15 (a mixture of 9:1 of the stereoisomer, predominantly as the cis diastereomer based on previously assigned for cyclobutanol 4) as a low-melting white solid: $R_f$=0.29 (20% EtOAc/Hex); m.p.=30-31° C.; IR (ZnSe, cm$^{-1}$) 3356 (br), 2922, 1734, 1154, 735, 696 cm$^{-1}$; $^1$H NMR: δ 7.40-7.30 (m, 5H), 5.11 (s, 2H), 4.42-4.34 (br m, 0.1H), 4.14-4.03 (br m, 0.9H), 2.48-2.40 (m, 0.18H), 2.35 (t, J=7.2, 0.18H), 2.16-2.04 (m, 0.2H), 1.95 (t, J=6.6, 0.2H), 1.70-1.56 (br m, 3H), 1.48-1.13 (br m, 12H); $^{13}$C NMR: δ 173.6, 136.0, 128.4, 128.1, 66.0, 63.7, 39.7, 37.0, 34.2, 29.2, 29.1, 29.0, 27.3, 25.4, 24.82; HRCI-MS: calcd. for $C_{19}H_{29}O_3Na$ $[M+Na]^+$: 305.2117. Found: 305.2116.

3-(Octanoic acid)cyclobutanol (11) was prepared similarly to compound 2. Benzyl ester DA6 (0.0337 g, 0.11 mmol), 10% Pd/C (0.0236 g, 0.022 mmol) and EtOAc (1 mL) were used to afford 0.0127 g of the unprotected acid 11 (54%) as a white solid: $R_f$=0.24 (6:4:0.05 of Hex:EtOAc:AcOH); m.p.=74-75° C.; IR (ZnSe, cm$^{-1}$) 3341 (br), 2916, 2849, 1695, 1064 cm$^{-1}$; $^1$H NMR (MeOD): δ 4.30 (quintet, J=6.8, 0.1H), 4.01 (quintet, J=6.4, 0.9H), 2.45-2.35 (br m, 2H), 2.29 (t, J=7.2, 2H), 1.75-1.55 (br m, 3H), 1.50-1.15 (br m, 12H); $^{13}$C NMR (MeOD): δ 176.3, 62.8, 38.9, 36.9, 36.8, 33.6, 29.1, 29.0, 28.8, 27.1, 25.4, 24.7; HRESI-MS: calcd. for $C_{12}H_{22}O_3Na$ $[M+Na]^+$: 237.1467. Found: 237.1460. Purity >97% by HPLC (retention time, 9.65 and 11.36 min).

Example 2—Determination of Inhibitor Aqueous Stability and Solubility

Although cyclobutenes are known to undergo thermally induced electrocyclic ring-opening, assessment of the thermal stability of cyclobutene using differential scanning calorimetry (DSC) and thermal gravimetric analysis (TGA) found no decomposition occurred at temperatures below 150° C. (FIG. 1).

One-dimensional (1D)$^1$H-NMR spectroscopy was used to verify the chemical purity, aqueous stability, and concentration dependent micelle formation of eleven fatty acid analogs. Each compound was dissolved in deuterated dimethyl sulfoxide (DMSO-$d_6$) to obtain a stock concentration of 20 mM. Four different concentrations were prepared from the stock solutions for NMR analysis: 1.00 mM, 750 μM, 500 μM, 100 μM. All NMR samples consisted of 600 μL of a deuterated 50 mM potassium phosphate buffer at pH 7.2 with 50 μM of 3 (trimethylsilyl) propionic-2,2,3,3-$d_4$ acid sodium salt (TMSP). Each 600 μL NMR sample contains 30 μL (5%) of DMSO-$d_6$ and was transferred to a 5 mm NMR tube for analysis.

A Bruker Avance DRX 500-MHz spectrometer equipped with a 5 mm triple-resonance cryoprobe ($^1$H, $^{13}$C, $^{15}$N) with a z-axis gradient was utilized for all 1D $^1$H NMR experiments. Acquisition of NMR spectra was automated using a BACS-120 sample changer and Icon NMR software. All spectra were acquired at 298.15 K with 16 dummy scans, 64 scans, 32K data points, a spectral width of 5482.46 Hz, and a relaxation delay of 1.5 s. The NMR spectra were processed and analyzed using ACD/1D NMR Manager (Advanced Chemistry Development). The resulting 1D $^1$H NMR spectra were visually inspected for evidence of micelle formation (peak broadening), or chemical instability/impurities (additional peaks).

Figure 2:
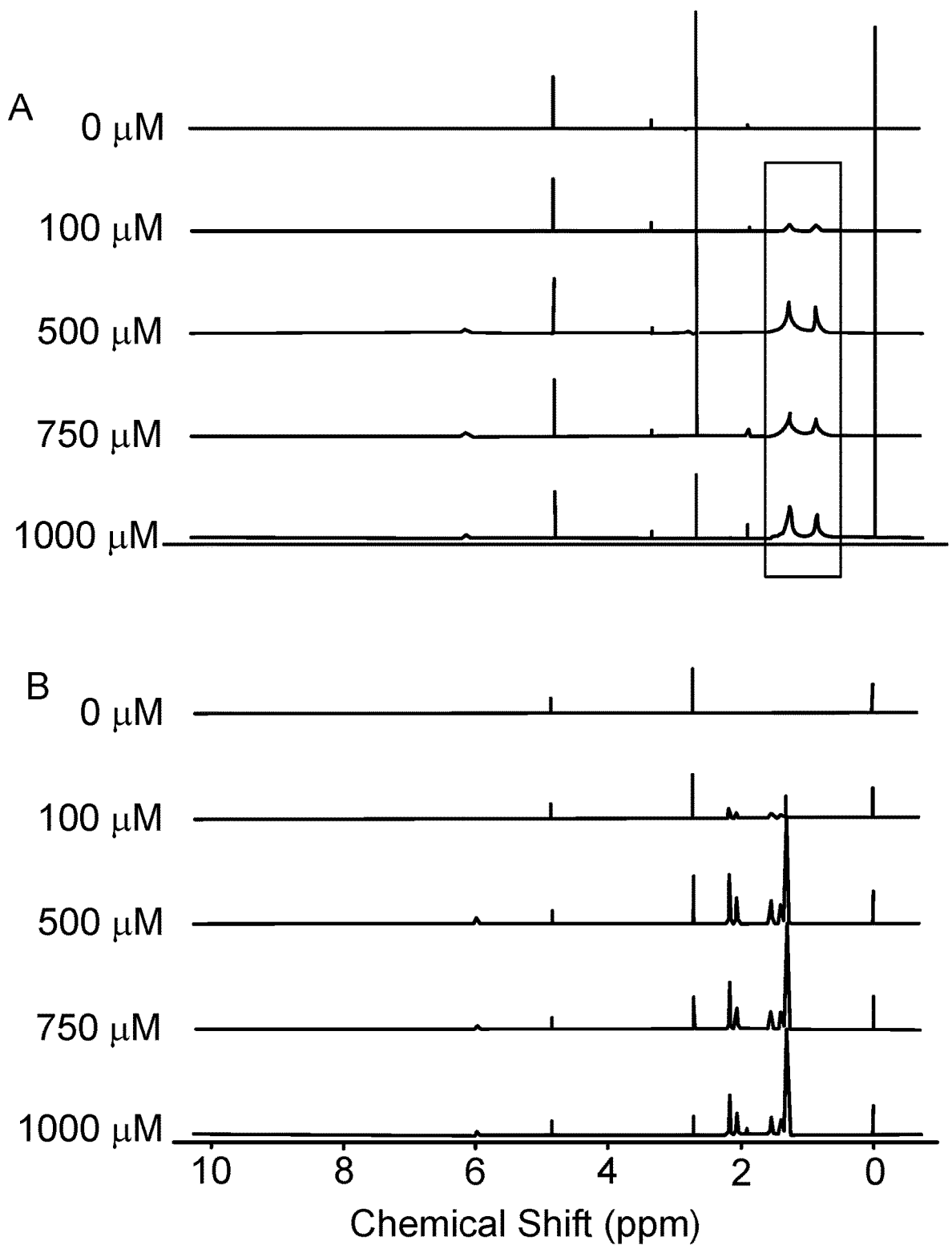
FIG. 2 shows 1D $^1$H NMR spectra of compounds (A) 1 and (B) 8 that were inspected for evidence of micelle formation (peak broadening) by comparing peak widths relative to TMSP (standard). Peak widths for compound 1 exhibited potential micelle formation or aggregation over the range of tested concentrations (highlighted region). No micelle formation was observed for compound 8 over the concentrations of 100 µM, 500 µM, 750 µM, and 1000 µM.

As exemplified in FIG. 2, the results demonstrate the analogs to be stable in aqueous buffer. The analogs based upon an octadecanoic acid (1, 2, 3, 4, 5, 6, and 7) scaffold aggregate at concentrations as low as 100 μM. The analogs based upon a decanoic acid backbone (8, 9, 10, and 11) do not form micelles or other aggregates at concentrations below 1 mM, the measured MICs (vida infra).

TABLE 1 critical micellar coefficient (CMC) of analogs under assay conditions[a]

| CMC     | ≥1000 μM         | ≤100 μM      |
|---------|------------------|--------------|
| Analogs | 1, 2, 3, 4, 5, 6, 7 | 8, 9, 10, 11 |

[a]Indicated concentration or range indicates onset of aggregation observed by $^1$H NMR of buffer solutions; see experimental

Example 3—Measurement of Nonspecific Cytotoxicity

RAW 264.7 macrophages were incubated with 0-100 μM of oleic acid or the C18 cyclobutene fatty acid 1, each delivered as bovine serum albumin complexes. After 24 h, cell viability was relative to untreated controls was assessed using an IN CTYOTOX-CVDE Crystal violet Dye Elution Kit.

Figure 4:
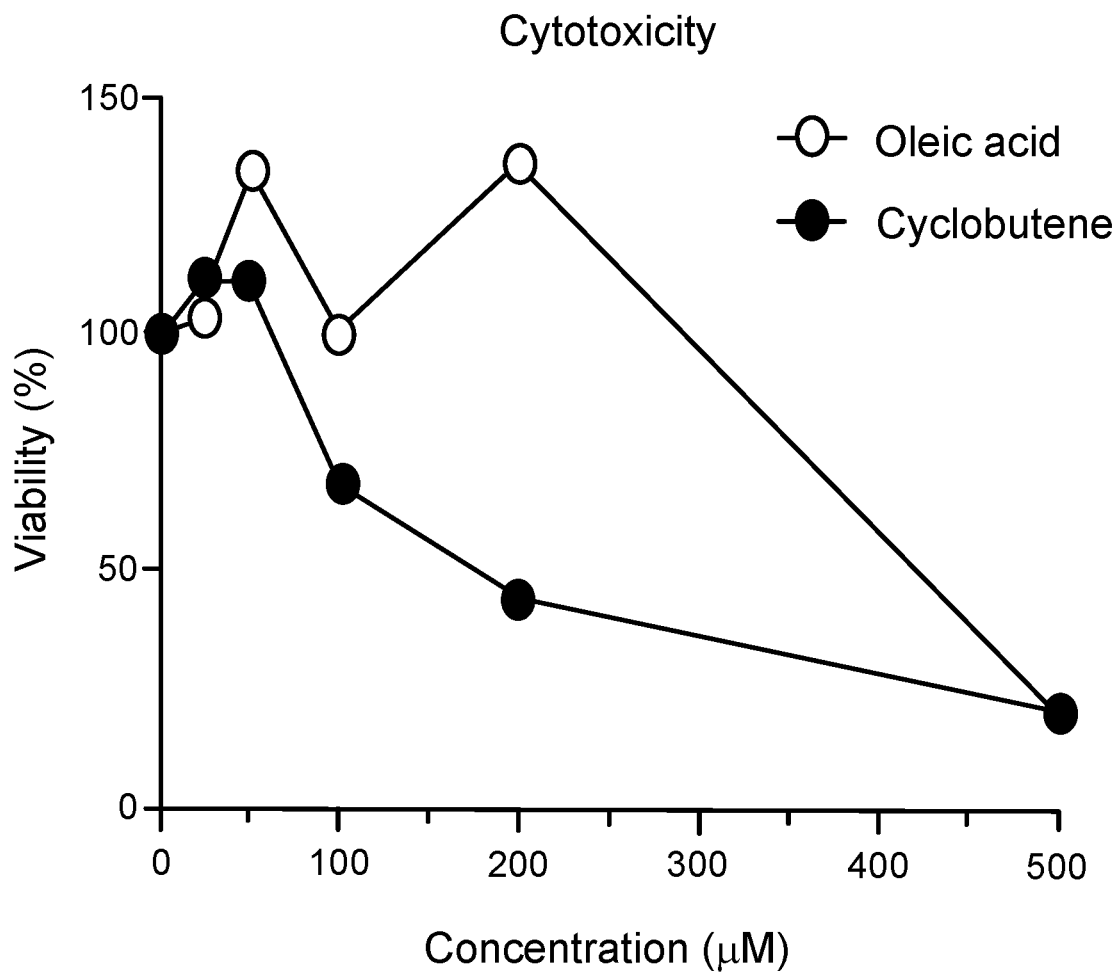
FIG. 4 illustrates the cytotoxicity of 1 measured in RAW 264.7 cells.

As illustrated in FIG. 4, the cyclobutene analogue 1 showed little toxicity at 50 μM and only modest toxicity at 100 μM; most naturally occurring fatty acids, represented here by oleate, display some toxicity this cell line at concentrations ≥200 μM (Russell, D. G. et al., Science 2010, 328: 852-856; and McShane, H., Trans. R. Soc. B 2011, 366, 2782-2789). The low toxicity against a mammalian cell line supports the potential investigations into the modified fatty acids as potential antimicrobials.

Example 4—Bacterial Strains and Culture Conditions

Bacterial strains used in this study are M. smeg (mc2155) and two strains of M. tb (CDC 1551 and H37Rv). Bacterial cells were grown with shaking at 37° C. in complete Middlebrook 7H9 broth supplemented with 0.05% v/v Tween 80 to an OD600 of 0.6-1.2. For MIC determinations, cells were inoculated into a modified previously reported minimal medium (Chacon et al 2002 REF) with components and final concentrations as follows: 22 mM dibasic potassium phosphate, 16 mM monobasic potassium phosphate, 2.8×10-5 mM ferric chloride, 8.7×10-3 mM zinc sulfate, 8.4×10-4 mM cobalt(II) chloride, 1.0×10-2 mM manganese chloride, 6.8×10-2 mM calcium chloride, 2.4 mM magnesium sulfate, 5.0 mM ammonium chloride, 25 mM glycerol, and 0.02% v/v Tyloxapol. The use of minimal media was dictated by preliminary experiments indicating that standard complete Middlebrook 7H9 media components may interfere with the MIC assay for some of these lipid analog compounds.

Example 5—Druz Susceptibility Assays

For MIC testing, each fatty acid analog compound was suspended in 100% DMSO-$d_6$ at either 100 mM (M. smeg) or 100 mg/ml (M. smeg and M. tb). An equivalent concentration DMSO-$d_6$ was tested separately. The concentration gradients, expressed in μg/ml (compound) and % DMSO-$d_6$, were generated using a power-2 series and varied between experiments. MICs were determined by a 96-well microplate twofold dilution method. Bacteria were harvested, washed 2× with minimal media, and inoculated to an initial concentration of approximately 1.0×105 colony forming units (CFU) per well. The initial inoculum was plated to verify retrospectively the desired CFU/ml for each strain. Plates were incubated at 37° C. for 3-4 day (M. smeg) or 5-7 weeks (M. tb). MIC values were determined by the consistent results of three biological and three technical replicates. The MIC was defined by taking the mode of three independent cultures where the MIC did not differ by more than one doubling dilution, discarding any results that are two doubling dilutions away from the mode.

Figure 3:
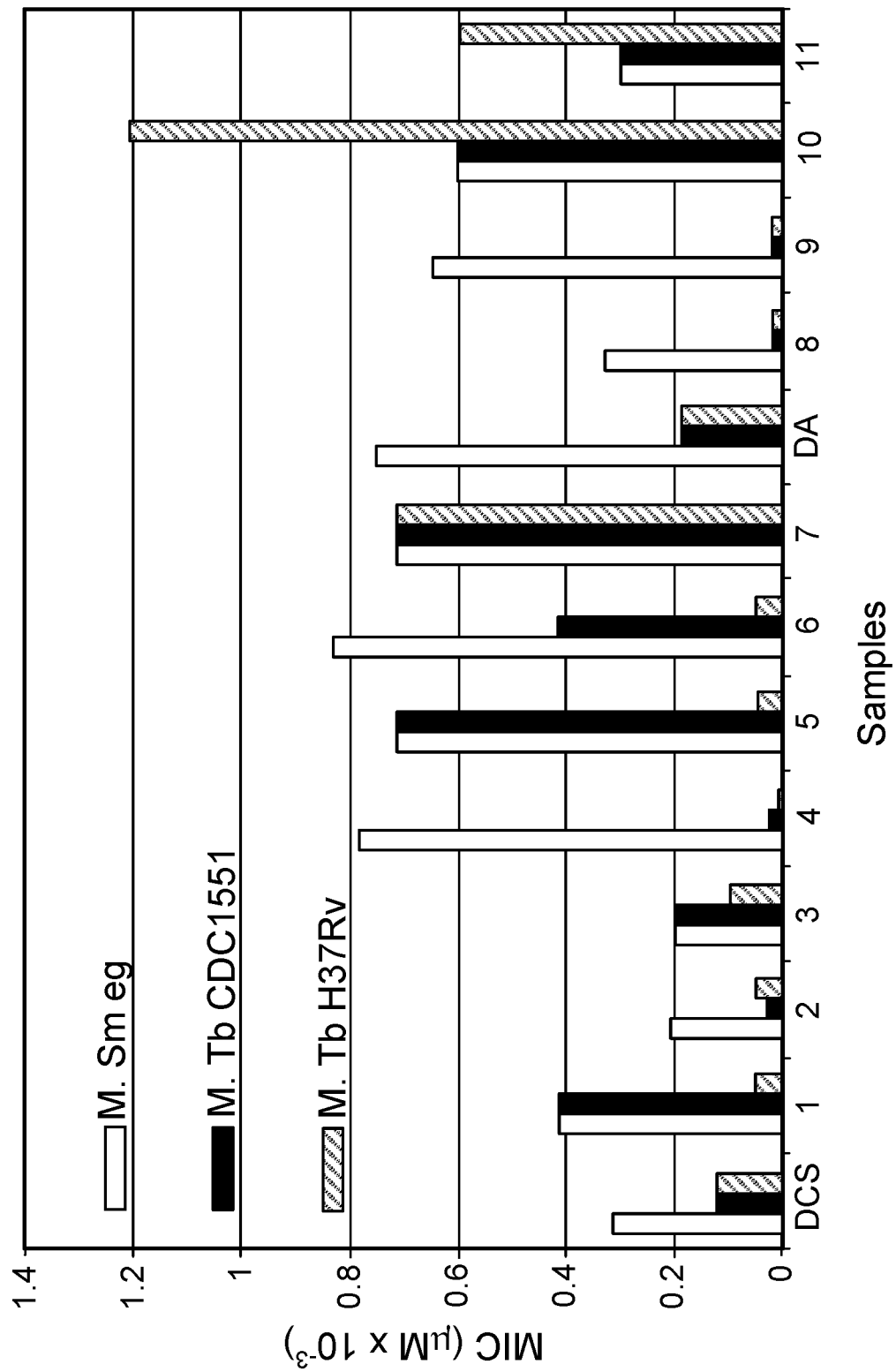
FIG. 3 shows the minimum inhibitory concentrations (MICS) of eleven analogs against *M. smeg.* (mc2155) and M. tb (CDC1551 and H37Rv).

MICs were initially determined against M. smeg (mc$^2$155), a non-pathogenic mycobacteria used as a model for M. tb to analyze processes that are likely to be conserved in the genus, and against two M. tb strains (CDC1551 and H37Rv). DSC, a clinically used TB drug, was employed as a control since MIC determinations for this compound have been standardized numerous times under different conditions in our laboratories. The analogs were added to wells as solutions in DMSO-$d_6$; the deuterated solvent was chosen for convenience to enable consistency with planned NMR-based metabolomics studies. Importantly, the DMSO-$d_6$ had no apparent effect on the growth of M. smeg, and contamination was not evident in the compound stock control wells or the media control wells. For M. tb, the combined analysis of 12 replicates for each of three independent cultures indicated no significant inhibition by DMSO-$d_6$ for either M. tb strain. Results for the fatty acid analogs are shown in Table 2 and FIG. 3. M. smeg was in general more resistant than M. tb to these analogs and DCS. The best MIC values against M. smeg were observed for 2, the $C_{18}$-cyclobutanone (3), 8, and the $C_{10}$-cyclobutanol 11, and were similar to the MIC for DCS (313 μM). Notably, four of the eleven molecules have MIC values <100 μM for both M. tb strains: these include the $C_{18}$ cyclobutane (2), the $C_{10}$ cyclobutene (8), the $C_{10}$ cyclobutane (9), and the $C_{18}$ cyclobutanol (4). These MIC values were lower than that measured (122 μM) for the second line antituberculosis drug D-cycloserine (DCS). Four other analogs yielded lower MICs compared with DCS in M. tb H37Rv; three others yielded higher MIC values than DCS.

TABLE 2

MIC values against M. smeg and M. tb

| Tested molecule[2] | M. smeg[1] (mc$^2$155) | | M. tb[1] (CDC1551) | | M. tb[1] (H37Rv) | |
|---|---|---|---|---|---|---|
| | MIC[3] (μg/ml) | MIC (μM) | MIC[4] (μg/ml) | MIC (μM) | MIC[4] (μg/ml) | MIC (μM) |
| DCS | 75 | 313 | 12.5 | 122 | 12.5 | 122 |
| 1 | 128 | 415 | 128 | 415 | 16 | 52 |
| 2 | 64 | 206 | 8 | 26 | 16 | 52 |
| 3 | 64 | 197 | 64 | 197 | 32 | 99 |
| 4 | 256 | 784 | 8 | 24 | 2 | 6 |
| 5 | 256 | 713 | 256 | 713 | 16 | 45 |
| 6 | 256 | 830 | 128 | 415 | 16 | 52 |
| 7 | 256 | 713 | 256 | 713 | 256 | 713 |
| Decanoic acid (DA) | 128 | 752 | 32 | 188 | 32 | 188 |
| 8 | 64 | 326 | 4 | 20 | 4 | 20 |
| 9 | 128 | 645 | 4 | 20 | 4 | 20 |
| 10 | 128 | 603 | 128 | 603 | 256 | 1,206 |
| 11 | 64 | 302 | 64 | 299 | 128 | 597 |

[1]Utilized 3 biological replicates and 3 technical replicates;
[2]All stocks are in 100% hexadeutero dimethyl sulfoxide (DMSO-$d_6$);
[3]The highest concentration tested was 1024 μg/ml;
[4]The highest concentration tested was 256 μg/ml The MIC results demonstrate promising levels of inhibition with a variety of four-membered ring carbocycles (cyclobutanol, cyclobutanone, cyclobutene, and cyclobutane). The measured MICs vary more than a hundred fold against M. tb H37Rv and more than thirty fold against strain CDC1551; a much smaller range is observed against *M. smeg*. Moreover, the nature of the functionality clearly has an impact on activity. The different influences of functionality within the C18 and C10 series are also notable; for example, the short-chain cyclobutanone (10) and cyclobutanol (11) are less potent toward mycobacteria than the corresponding long-chain analogs (3 and 4), while the opposite trend is observed with the cyclobutenes (8 vs. 1 or 6) or cyclobutanes (9 vs. 2 or 7). The cis/trans configuration of the four-membered carbocycle (monochlorocyclobutanones 5 vs. 7) appears to have a substantial influence on MICs for M. tb. (H37Rv); however, no different is observed for cyclobutenes 1 and 6.

Most of our analogs (8 out of 11) show lower MIC values in M. tb than *M. smeg*. The five to ten fold differences between MICs for *M. smeg* and M. tb with some analogs (2, 4, 6, 8 and 9) may result from a mechanism of action specific to M. tb. Isoniazid, for example, demonstrates 100-fold more potent inhibition of M. tb compared with *M. smeg* and possesses no toxicity toward other mycobacteria and prokaryotic pathogens. The influence of the analogs may be specific to a metabolic pathway only found in M. tb such as at the final elongation step. It is also possible that our four-membered ring analogs are converted into analogs of mycolic acids and that the physical properties of these unnatural cell wall constituents results in cell death.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound of Formula (I):

or a pharmaceutically acceptable salt thereof,
wherein:
----- represents an optionally present double bond;
$R^1$ and $R^2$ are independently selected from the group consisting of: H, halo, $OR^5$, and =O;
$R^3$ is an optionally substituted $C_5$-$C_{40}$ alkyl;
$R^4$ is $C_2$-$C_{30}$ alkyl optionally substituted with $Cy^1$, $C_{1-6}$ alkyl, $C_{2-6}$ alkenyl, $C_{2-6}$ alkynyl, halo, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$;
each $Cy^1$ is independently $C_{6-10}$ aryl, $C_{3-10}$ carbocyclyl, 5-10 membered heteroaryl or 4-10 membered heterocyclyl, each of which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$ and oxo;
each $R^{a1}$, $R^{b1}$, $R^{c1}$, $R^{d1}$, is independently selected from $C_{1-4}$ haloalkyl, $C_{2-6}$ alkenyl, $C_{2-6}$ alkynyl, $C_{6-10}$ aryl, $C_{3-10}$ carbocyclyl, 5-10 membered heteroaryl, 4-10 membered heterocyclyl, $C_{6-10}$ aryl-$C_{1-4}$ alkyl, $C_{3-10}$ carbocyclyl-$C_{1-4}$ alkyl, (5-10 membered heteroaryl)-$C_{1-4}$ alkyl or (4-10 membered heterocyclyl)-$C_{1-4}$ alkyl, wherein said $C_{2-6}$ alkenyl, $C_{2-6}$ alkynyl, $C_{6-10}$ aryl, $C_{3-10}$ carbocyclyl, 5-10 membered heteroaryl, 4-10 membered heterocyclyl, $C_{6-10}$ aryl-$C_{1-4}$ alkyl, $C_{3-10}$ carbocyclyl-$C_{1-4}$ alkyl, (5-10 membered heteroaryl)-$C_{1-4}$ alkyl and (4-10 membered heterocyclyl)-$C_{1-4}$ alkyl is optionally substituted with 1, 2, 3, 4, or 5 substituents independently selected from $C_{1-4}$ alkyl, $C_{1-4}$ haloalkyl, halo, CN, $OR^{a4}$, $SR^{a4}$, $C(O)R^{b4}$, $C(O)NR^4R^{d4}$, $C(O)OR^{a4}$, $OC(O)R^{b4}$, $OC(O)NR^{c4}R^{d4}$, $NR^4R^{d4}$, $NR^{c4}C(O)R^{b4}$, $NR^{c4}C(O)NR^4R^{d4}$, $NR^{c4}C(O)OR^{a4}$, $C(=NR^{e4})NR^4R^{d4}$, $NR^{c4}C(=NR^{e4})NR^{c4}R^{d4}$, $S(O)R^{b4}$, $S(O)NR^4R^{d4}$, $S(O)_2R^{b4}$, $NR^{c4}S(O)_2R^{b4}$, $NR^{c4}S(O)_2NR^4R^{d4}$ and $S(O)_2NR^4R^{d4}$;
each $R^{a4}$, $R^{b4}$, $R^{c4}$ and $R^{d4}$ is independently selected from H, $C_{1-4}$ alkyl, $C_{1-4}$ haloalkyl, $C_{2-4}$ alkenyl and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and
Z is selected from the group consisting of: $COR^6$, $CO_2H$, $NHC(O)NR^6R^7$, $CONR^6$, $OCOR^6$, $OR^6$, $SR^6$, $NR^6R^7$, and $OPO_3R^6$;
$R^5$ is $C_1$-$C_6$ alkyl;
$R^6$ and $R^7$ are independently H or $C_1$-$C_6$ alkyl; and
wherein the hydrocarbon backbone formed by $R^4$ and $R^3$—Z is amphiphilic.

2. The compound of claim 1, wherein $R^1$ and $R^2$ are independently selected from the group consisting of: H, halo, and =O.

3. The compound of claim 1, wherein the compound is selected from the group consisting of:

or a pharmaceutically acceptable salt thereof.

4. The compound of claim 1, wherein $R^4$ is a $C_2$-$C_{10}$ alkyl.

5. The compound of claim 1, wherein Z is CO$_2$H.

6. The compound of claim 1, wherein the compound is a compound of Formula (II):

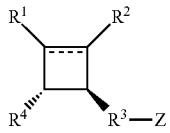

or a pharmaceutically acceptable salt thereof.

7. The compound of claim 1, wherein the compound is a compound of Formula (III):

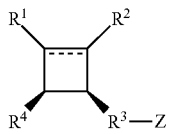

or a pharmaceutically acceptable salt thereof.

8. The compound of claim 1, wherein the compound is selected from the group consisting of:

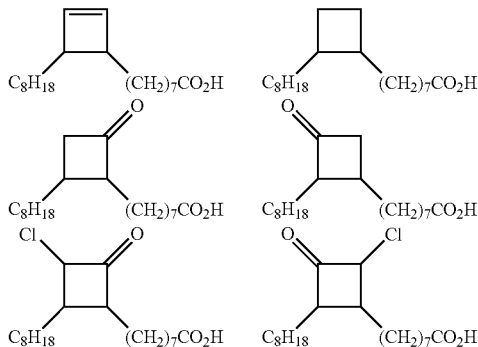

or a pharmaceutically acceptable salt thereof.

9. The compound of claim 8, wherein the compound is selected from the group consisting of:

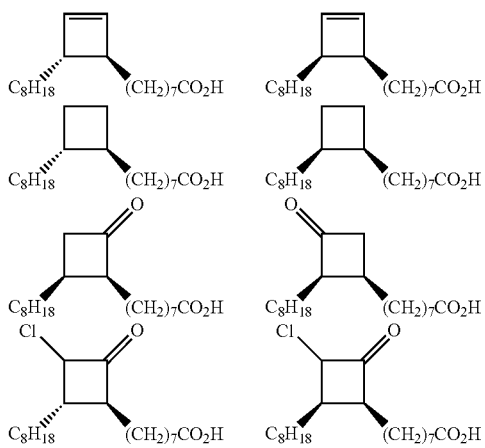

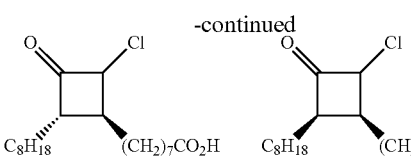

or a pharmaceutically acceptable salt thereof.

10. A pharmaceutical composition comprising a compound of Formula (I):

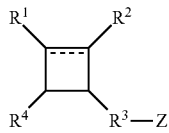

or a pharmaceutically acceptable salt thereof,
wherein:

---- represents an optionally present double bond;

R$^1$ and R$^2$ are independently selected from the group consisting of: H, halo, OR$^5$, and =O;

R$^3$ is an optionally substituted C$_5$-C$_{40}$ alkyl;

R$^4$ is C$_1$-C$_{40}$ alkyl optionally substituted with Cy$^1$, C$_{1-6}$ alkyl, C$_{2-6}$ alkenyl, C$_{2-6}$ alkynyl, halo, C$_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$ S(O)$_2$R$^{b1}$ and S(O)$_2$NR$^{c1}$R$^{d1}$;

each Cy$^1$ is independently C$_{6-10}$ aryl, C$_{3-10}$ carbocyclyl, 5-10 membered heteroaryl or 4-10 membered heterocyclyl, each of which is unsubstituted or substituted by 1, 2, 3, 4 or 5 substituents independently selected from C$_{1-6}$ alkyl, C$_{2-6}$ alkenyl, C$_{2-6}$ alkynyl, halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, S(O)$_2$NR$^{c1}$R$^{d1}$ and oxo;

each R$^{a1}$, R$^{b1}$, R$^{c1}$, R$^{d1}$, is independently selected from C$_{1-4}$ haloalkyl, C$_{2-6}$ alkenyl, C$_{2-6}$ alkynyl, C$_{6-10}$ aryl, C$_{3-10}$ carbocyclyl, 5-10 membered heteroaryl, 4-10 membered heterocyclyl, C$_{6-10}$ aryl-C$_{1-4}$ alkyl, C$_{3-10}$ carbocyclyl-C$_{1-4}$ alkyl, (5-10 membered heteroaryl)-C$_{1-4}$ alkyl or (4-10 membered heterocyclyl)-C$_{1-4}$ alkyl, wherein said C$_{2-6}$ alkenyl, C$_{2-6}$ alkynyl, C$_{6-10}$ aryl, C$_{3-10}$ carbocyclyl, 5-10 membered heteroaryl, 4-10 membered heterocyclyl, C$_{6-10}$ aryl-C$_{1-4}$ alkyl, C$_{3-10}$ carbocyclyl-C$_{1-4}$ alkyl, (5-10 membered heteroaryl)-C$_{1-4}$ alkyl and (4-10 membered heterocyclyl)-C$_{1-4}$ alkyl is optionally substituted with 1, 2, 3, 4, or 5 substituents independently selected from C$_{1-4}$ alkyl, C$_{1-4}$ haloalkyl, halo, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{e4}$)NR$^{c4}$R$^{d4}$, NR$^{c4}$C(=NR$^{e4}$)NR$^{c4}$R$^{d4}$, S(O)R$^{b4}$, S(O)NR$^{c4}$R$^{d4}$, S(O)$_2$R$^{b4}$ NR$^{c4}$S(O)$_2$R$^{b4}$, NR$^{c4}$S(O)$_2$NR$^{c4}$R$^{d4}$ and S(O)$_2$NR$^{c4}$R$^{d4}$;

each R$^{a4}$, R$^{b4}$, R$^{c4}$ and R$^{d4}$ is independently selected from H, C$_{1-4}$ alkyl, C$_{1-4}$ haloalkyl, C$_{2-4}$ alkenyl and C$_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and Z is selected from the group consisting of: $COR^6$, $CO_2H$, $CONR^6$, $OCOR^6$, $OR^6$, $SR^6$, $NR^6R^7$, and $OPO_3R^6$;

$R^5$ is $C_1$-$C_6$ alkyl;

$R^6$ and $R^7$ are independently H or $C_1$-$C_6$ alkyl; and wherein the hydrocarbon backbone formed by $R^4$ and $R^3$—Z is amphiphilic and a pharmaceutically acceptable carrier.

11. A method for treating a mycobacterial infection in a patient, the method comprising administering to the patient a therapeutically effective amount of a compound of Formula (I):

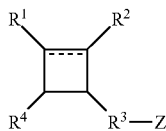

or a pharmaceutically acceptable salt thereof, wherein:

----- represents an optionally present double bond;

$R^1$ and $R^2$ are independently selected from the group consisting of: H, halo, $OR^5$, and =O;

$R^3$ is absent or is an optionally substituted $C_1$-$C_{40}$ alkyl;

$R^4$ is H or an optionally substituted $C_1$-$C_{40}$ alkyl; and

Z is selected from the group consisting of: $COR^6$, $C_{O2}R^6$, $CONR^6$, $OCOR^6$, $OR^6$, $SR^6$, $NR^6R^7$, and $OPO_3R^6$;

$R^5$ is H or $C_1$-$C_6$ alkyl;

$R^6$ and $R^7$ are independently H or $C_1$-$C_6$ alkyl;

wherein the backbone formed by $R^4$ and $R^3$—Z is amphiphilic.

12. The method of claim 11, wherein the mycobacterial infection is a member of a group selected from: *Mycobacterium tuberculosis* complex (MTBC), *Mycobacterium avium* complex (MAC), *Mycobacterium gordonae* clade, *Mycobacterium kansasii* clade, *Mycobacterium nonchromogenicum/terrae* clade, Mycolactone-producing mycobacteria, *Mycobacterium simiae* clade, *Mycobacterium chelonae* clade, *Mycobacterium abscessus*, *Mycobacterium chelonae*, *Mycobacterium bolletti*, *Mycobacterium fortuitum* clade, *Mycobacterium parafortuitum* clade, *Mycobacterium vaccae* clade, and CF.

13. The method of claim 11, wherein the mycobacterial infection is *M. tuberculosis*.

14. The compound of claim 1, wherein $R^4$ is a $C_5$-$C_{20}$ alkyl.

15. The compound of claim 1, wherein $R^4$ is a $C_{10}$-$C_{30}$ alkyl.

16. The compound of claim 1, wherein $R^4$ is a $C_2$-$C_8$ alkyl.

17. The compound of claim 1, wherein $R^4$ is a $C_8$ alkyl.

18. A compound selected from the group consisting of:

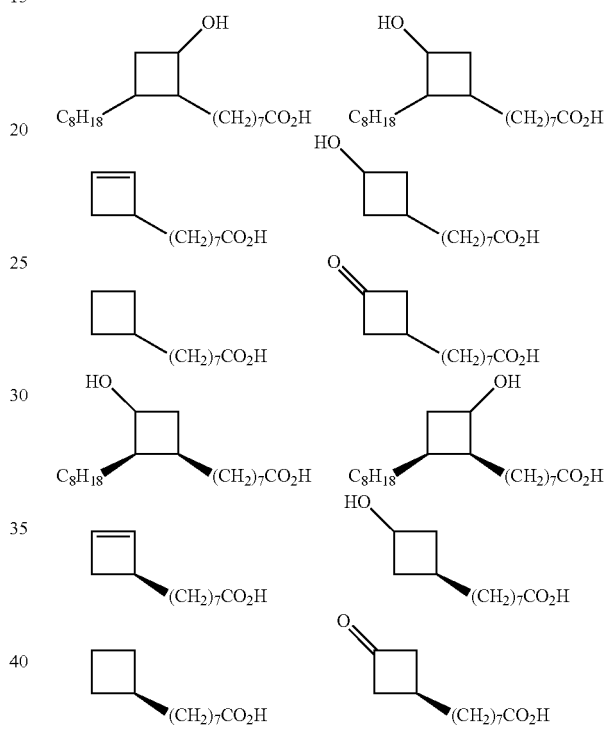

or a pharmaceutically acceptable salt thereof.

* * * * *

UNITED STATES PATENT AND TRADEMARK OFFICE
CERTIFICATE OF CORRECTION

PATENT NO. : 10,538,475 B2
APPLICATION NO. : 14/403763
DATED : January 21, 2020
INVENTOR(S) : Wantanee Sittiwong et al.

Page 1 of 2

It is certified that error appears in the above-identified patent and that said Letters Patent is hereby corrected as shown below:

On the Title Page

Column 1 (Title) Line 2 Delete "CYLOBUTANES" and insert -- CYCLOBUTANES --, therefor.

Column 2 (Other Publications) Line 4 Delete "frans" and insert -- trans --, therefor.

In the Specification

Column 1 Line 12 after "2012," delete "both of".

In the Claims

Column 49 Line 61 In Claim 1, after "S(O)NR$^{c1}$R$^{d1}$" insert -- , --.

Column 50 Line 6 In Claim 1, after "S(O)R$^{b1}$" insert -- , --.

Column 50 Line 23 (approx.) In Claim 1, delete "C(O)NR$^{4}$R$^{d4}$," and insert -- C(O)NR$^{c4}$R$^{d4}$, --, therefor.

Column 50 Line 24 (approx.) In Claim 1, delete "NR$^{4}$R$^{d4}$," and insert -- NR$^{c4}$R$^{d4}$ --, therefor.

Column 50 Line 24-25 In Claim 1, delete "NR$^{c4}$C(O)NR$^{4}$R$^{d4}$," and insert -- NR$^{c4}$C(O)NR$^{c4}$R$^{d4}$, --, therefor.

Column 52 Line 24 In Claim 10, please delete "and =0" and insert -- and =O --, therefor.

Column 50 Line 25 (approx.) In Claim 1, delete "C(=NR$^{e4}$)NR$^{4}$R$^{d4}$," and insert -- C(=NR$^{e4}$)NR$^{c4}$R$^{d4}$, --, therefor.

Signed and Sealed this
Thirtieth Day of June, 2020

Andrei Iancu
*Director of the United States Patent and Trademark Office*

CERTIFICATE OF CORRECTION (continued)
U.S. Pat. No. 10,538,475 B2

Column 50 Line 26 In Claim 1, delete "S(O)NR$^4$R$^{d4}$," and insert -- S(O)NR$^{c4}$R$^{d4}$, --, therefor.

Column 50 Line 27 In Claim 1, after "S(O)2R$^{b4}$" insert -- , --.

Column 50 Line 27 In Claim 1, delete "NR$^{c4}$S(O)$_2$NR$^4$R$^{d4}$" and insert -- NR$^{c4}$S(O)$_2$NR$^{c4}$R$^{d4}$ --, therefor.

Column 50 Line 28 (approx.) In Claim 1, delete "S(O)$_2$NR$^4$R$^{d4}$;" and insert -- S(O)$_2$NR$^{c4}$R$^{d4}$; --, therefor.

Column 52 Line 32 In Claim 10, after "S(O)NRc1Rd1" insert -- , --.

Column 52 Line 60 In Claim 10, delete "C(O)NR$^4$R$^{d4}$," and insert -- C(O)NR$^{c4}$R$^{d4}$, --, therefor.

Column 52 Line 61 In Claim 10, delete "NR$^4$R$^{d4}$," and insert -- NR$^{c4}$R$^{d4}$, --, therefor.

Column 52 Line 61-62 In Claim 10, delete "NR$^{c4}$C(O)NR$^4$R$^{d4}$," and insert -- NR$^{c4}$C(O)NR$^{c4}$R$^{d4}$, --, therefor.

Column 52 Line 63 In Claim 10, delete "C(=NR$^{e4}$)NR$^4$R$^{d4}$," and insert -- C(=NR$^{e4}$)NR$^{c4}$R$^{d4}$, --, therefor.

Column 52 Line 62 In Claim 10, delete "NR$^{c4}$C(=NR$^{e4}$)NR$^4$R$^{d4}$" and insert -- NR$^{c4}$C(=NR$^{e4}$)NR$^{c4}$R$^{d4}$, --, therefor.

Column 52 Line 62 In Claim 10, delete "S(O)NR$^4$R$^{d4}$," and insert -- S(O)NR$^{c4}$R$^{d4}$, --, therefor.

Column 52 Line 64 In Claim 10, after "S(O)$_2$R$^{b4}$" insert -- , --.

Column 52 Line 64 In Claim 10, delete "NR$^{c4}$S(O)$^2$NR$^4$R$^{d4}$" and insert -- NR$^{c4}$S(O)$_2$NR$^{c4}$R$^{d4}$ --, therefor.

Column 52 Line 65 In Claim 10, delete "S(O)2NR4Rd4;" and insert -- S(O)$_2$NR$^{c4}$R$^{d4}$; --, therefor.

Column 53 Line 33 In Claim 11, please delete "CO2R6" and insert -- CO$_2$R$^6$ --, therefor.

Column 54 Line 1 In Claim 12, delete "bolletti," and insert -- bolletii, --, therefor.